US010265525B2

(12) United States Patent
Courtine et al.

(10) Patent No.: US 10,265,525 B2
(45) Date of Patent: Apr. 23, 2019

(54) SYSTEM TO DELIVER ADAPTIVE EPIDURAL AND/OR SUBDURAL ELECTRICAL SPINAL CORD STIMULATION TO FACILITATE AND RESTORE LOCOMOTION AFTER A NEUROMOTOR IMPAIRMENT

(71) Applicant: ECOLE POLYTECHNIQUE FEDERALE DE LAUSANNE (EPFL), Lausanne (CH)

(72) Inventors: Gregoire Courtine, Lausanne (CH); Nikolaus Wenger, Pully (CH); Eduardo Martin Moraud, Pully (CH); Silvestro Micera, St-sulpice VD (CH); Marco Bonizzato, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/033,063

(22) PCT Filed: Oct. 29, 2014

(86) PCT No.: PCT/EP2014/073183
§ 371 (c)(1),
(2) Date: Apr. 28, 2016

(87) PCT Pub. No.: WO2015/063127
PCT Pub. Date: May 7, 2015

(65) Prior Publication Data
US 2016/0279418 A1    Sep. 29, 2016

(30) Foreign Application Priority Data

Oct. 31, 2013    (EP) .................................... 13191003

(51) Int. Cl.
*A61B 5/04*    (2006.01)
*A61B 5/11*    (2006.01)
(Continued)

(52) U.S. Cl.
CPC ...... *A61N 1/36067* (2013.01); *A61B 5/04001* (2013.01); *A61B 5/0476* (2013.01);
(Continued)

(58) Field of Classification Search
CPC .............. A61N 1/36067; A61N 1/0551; A61N 1/36003; A61N 1/36103; A61N 1/36135;
(Continued)

(56) References Cited

U.S. PATENT DOCUMENTS 8,374,696 B2    2/2013  Sanchez et al.
2002/0115945 A1  8/2002  Herman et al.
(Continued)

FOREIGN PATENT DOCUMENTS

EP    2486897 A2    8/2012
EP    2628502 A1    8/2013
(Continued)

OTHER PUBLICATIONS

Abbas et al. "Neural Network Control of Functional Neuromuscular Stimulation Systems: Computer Simulation Studies", IEEE Transactions on Biomedical Engineering, Vo. 42, No. 11, Nov. 1995.*
(Continued)

*Primary Examiner* — Carl H Layno
*Assistant Examiner* — Erin M Piateski
(74) *Attorney, Agent, or Firm* — McCoy Russell LLP

(57) ABSTRACT

The present invention provides a closed-loop system for real-time control of epidural and/or subdural electrical stimulation comprising: means for applying to a subject neuromodulation with adjustable stimulation parameters, said means being operatively connected with a real-time monitoring component comprising sensors continuously acquiring feedback signals from said subject, said signals being neural signals and/or signals providing features of motion of said subject, said system being operatively con-
(Continued)

nected with a signal processing device receiving said feedback signals and operating real-time automatic control algorithms, said signal processing device being operatively connected with said means and providing said means with new stimulation parameters, with minimum delay. The system of the invention improves consistency of walking in a subject with a neuromotor impairment. A Real Time Automatic Control Algorithm is used, comprising a feedforward component employing a single input-single output model (SISO), or a multiple input-single output (MISO) model.

16 Claims, 12 Drawing Sheets

(51) Int. Cl.
    A61N 1/05      (2006.01)
    A61B 5/0476    (2006.01)
    A61B 5/0488    (2006.01)
    A61N 1/36      (2006.01)
    A61B 5/00      (2006.01)
(52) U.S. Cl.
    CPC ............ A61B 5/0488 (2013.01); A61B 5/112
        (2013.01); A61B 5/1121 (2013.01); A61B
        5/1127 (2013.01); A61B 5/4836 (2013.01);
        A61B 5/7282 (2013.01); A61N 1/0551
        (2013.01); A61N 1/36003 (2013.01); A61N
        1/36103 (2013.01); A61N 1/36135 (2013.01);
        A61N 1/36139 (2013.01); A61B 2562/0219
        (2013.01); A61B 2562/0247 (2013.01)
(58) Field of Classification Search
    CPC ............ A61N 1/36139; A61B 5/04001; A61B
        5/0476; A61B 5/0488; A61B 5/112; A61B
        5/1121; A61B 5/1127; A61B 5/4836;
        A61B 5/7282; A61B 2562/0219; A61B
        2562/024
    USPC .......................................................... 607/39
    See application file for complete search history.

(56) References Cited

U.S. PATENT DOCUMENTS

| 2003/0114894 | A1 | 6/2003 | Dar et al. |
| 2004/0267320 | A1 | 12/2004 | Taylor et al. |
| 2005/0090756 | A1 | 4/2005 | Wolf et al. |
| 2007/0004567 | A1 | 1/2007 | Shetty et al. |
| 2007/0067003 | A1 | 3/2007 | Sanchez et al. |
| 2007/0179534 | A1* | 8/2007 | Firlik ................ A61M 5/14276 607/3 |
| 2011/0208265 | A1 | 8/2011 | Erickson et al. |
| 2012/0330391 | A1 | 12/2012 | Bradley et al. |
| 2013/0138167 | A1 | 5/2013 | Bradley et al. |
| 2014/0163640 | A1* | 6/2014 | Edgerton ............. A61N 1/0551 607/48 |

FOREIGN PATENT DOCUMENTS

| WO | 2007047852 | A2 | 4/2007 |
| WO | 2012094346 | A2 | 7/2012 |
| WO | 2013071309 | A1 | 5/2013 |

OTHER PUBLICATIONS

Ichiyama, R. et al., "Hindlimb stepping movements in complete spinal rats induced by epidural spinal cord stimulation," Neuroscience Letters, vol. 383, No. 3, Aug. 5, 2005, 6 pages.
Minassian K. et al., "Human lumbar cord circuitries can be activated by extrinsic tonic input to generate locomotor-like activity," Human Movement Science, vol. 26, No. 2, Apr. 2007, Published Online Mar. 6, 2007, 21 pages.
Gerasimenko, Y. et al., "Epidural Spinal Cord Stimulation Plus Quipazine Administration Enable Stepping in Complete Spinal Adult Rats," Journal of Neurophysiology, vol. 98, No. 5, Nov. 2007, Published Online Sep. 12, 2007, 12 pages.
Edgerton, V. et al., "Training locomotor networks," Brain Research Reviews, vol. 57, No. 1, Jan. 2008, Published Online Sep. 16, 2007, 14 pages.
Ichiyama, R. et al., "Step Training Reinforces Specific Spinal Locomotor Circuitry in Adult Spinal Rats," The Journal of Neuroscience, vol. 28, No. 29, Jul. 16, 2008, 6 pages.
Keller, U., "Construction and Control of a Multi-Directional Support System for Neurorehabilitation of Spinal Cord Injured Rats," Master Thesis in Mechanical Engineering, ETH Zurich, Jul. 1, 2009, 88 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Harkema, S. et al., "Effect of epidural stimulation of the lumbosacral spinal cord on voluntary movement, standing, and assisted stepping after motor complete paraplegia: a case study," vol. 377, No. 9781, Jun. 4, 2011, Published Online May 20, 2011, 10 pages.
Musienko, P. et al., "Multi-system neurorehabilitative strategies to restore motor functions following severe spinal cord injury," Experimental Neurology, vol. 235, No. 1, May 2012, Published Online Sep. 7, 2011, 10 pages.
Dominici, N. et al., "Versatile robotic interface to evaluate, enable and train locomotion and balance after neuromotor disorders," Nature Medicine, vol. 18, No. 7, Jul. 2012, Published Online May 31, 2012, 8 pages.
Van Den Brand, R. et al., "Restoring Voluntary Control of Locomotion after Paralyzing Spinal Cord Injury," vol. 336, No. 6085, Jun. 1, 2012, 4 pages.
Borton, D. et al., "Corticospinal neuroprostheses to restore locomotion after spinal cord injury," Neuroscience Research, vol. 78, Jan. 2014, Published Online Oct. 14, 2013, 9 pages.
ISA European Patent Office, International Search Report Issued in Application No. PCT/EP2014/073183, dated Jan. 23, 2015, WIPO, 4 pages.
Guyatt, G. et al., "The 6-minute walk: a new measure of exercise capacity in patients with chronic heart failure," Canadian Medical Association Journal, vol. 132, No. 8, Apr. 15, 1985, 5 pages.
Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER x95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.

(56) References Cited

OTHER PUBLICATIONS

Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusc to Man—G.N. Orlovsky, T.G. Deliagina and S. Grinner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.
Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine G. et al., "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K. et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury", Nature Neuroscience, vol. 12, No. 9, Sep. 2009, Published Online Aug. 2, 2009, 22 pages.
Hagglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.

(56) References Cited

OTHER PUBLICATIONS

Sun, F. et al., "Sustained axon regeneration induced by co-deletion of PTEN and SOCS3," Nature, vol. 480, No. 7377, Dec. 15, 2011, Published Online Nov. 6, 2011, 12 pages.

* cited by examiner

SYSTEM TO DELIVER ADAPTIVE EPIDURAL AND/OR SUBDURAL ELECTRICAL SPINAL CORD STIMULATION TO FACILITATE AND RESTORE LOCOMOTION AFTER A NEUROMOTOR IMPAIRMENT

CROSS REFERENCE TO RELATED APPLICATIONS

The present application is a U.S. National Phase of International Patent Application Ser. No. PCT/EP2014/073183, entitled "SYSTEM TO DELIVER ADAPTIVE EPIDURAL AND/OR SUBDURAL ELECTRICAL SPINAL CORD STIMULATION TO FACILITATE AND RESTORE LOCOMOTION AFTER A NEUROMOTOR IMPAIRMENT," filed on Oct. 29, 2014, which claims priority to European Patent Application No. 13191003.6, entitled "SYSTEM TO DELIVER ADAPTIVE ELECTRICAL SPINAL CORD STIMULATION TO FACILITATE AND RESTORE LOCOMOTION AFTER A NEUROMOTOR IMPAIRMENT," filed on Oct. 31, 2013, the entire contents of each of which are hereby incorporated by reference for all purposes.

FIELD OF THE INVENTION

The present invention refers to the field of neuroprosthetics, in particular to devices and systems for facilitating and restoring locomotion in subjects after neurological disorders, more in particular after spinal cord injury (SCI), Parkinson's disease, multiple sclerosis, and stroke.

BACKGROUND OF INVENTION

Epidural electrical spinal cord stimulation (EES) at the lumbosacral segments has been shown to be a very promising intervention capable of facilitating locomotion in rats, cats, and humans with SCI (Ichiyama, R. M., Gerasimenko, Y. P., Zhong, H., Roy, R. R. & Edgerton, V. R. Hindlimb stepping movements in complete spinal rats induced by epidural spinal cord stimulation. Neuroscience letters 383, 339-344, doi:10.1016/j.neulet.2005.04.049 (2005); Minassian, K. et al. Human lumbar cord circuitries can be activated by extrinsic tonic input to generate locomotor-like activity. Human movement science 26, 275-295, doi: 10.1016/j.humov.2007.01.005 (2007); Harkema, S. et al. Effect of epidural stimulation of the lumbosacral spinal cord on voluntary movement, standing, and assisted stepping after motor complete paraplegia: a case study. The Lancet 377, 1938-1947 (2011); Gerasimenko, Y. P. et al. Epidural spinal cord stimulation plus quipazine administration enable stepping in complete spinal adult rats. J Neurophysiol 98, 2525-2536, doi:10.1152/jn.00836.2007 (2007)).

When combined with pharmacological interventions and locomotor training, EES was demonstrated to affect functional recovery, i.e., spinal rats were able to recover full weight-bearing stepping capacities on a treadmill (Edgerton, V. R. et al. Training locomotor networks. Brain research reviews 57, 241-254, doi:10.1016/j.brainresrev.2007.09.002 (2008); Ichiyama, R. M. et al. Step training reinforces specific spinal locomotor circuitry in adult spinal rats. The Journal of neuroscience: the official journal of the Society for Neuroscience 28, 7370-7375, doi:10.1523/JNEUROSCI.1881-08.2008 (2008); Courtine, G. et al. Transformation of nonfunctional spinal circuits into functional states after the loss of brain input. Nature neuroscience 12, 1333-1342, doi:10.1038/nn.2401 (2009); Musienko, P., Heutschi, J., Friedli, L., den Brand, R. V. & Courtine, G. Multi-system neurorehabilitative strategies to restore motor functions following severe spinal cord injury. Experimental neurology, doi:10.1016/j.expneurol.2011.08.025 (2011)).

In the prior art several patents regarding neuroprosthetic apparatus or systems can be found.

US2005/090756 discloses a neural spike detection system for neuroprosthetic control, wherein neural signals are received and an information signal is transmitted when a neural spike is detected.

US2004/0267320 discloses algorithm for programming a device according to the firing rate of motor neurons. In particular, electrical impulses are detected and movements are calculated from said impulses. Said impulses are preferably detected in a subject cerebral cortex and brain-to-arm control is preferably provided.

US2003/114894 discloses a surface neuroprosthetic that enables facile adjustment and fine-tuning of the local current density over the surface of a transcutaneous scanning electrode, so as to achieve optimal muscle response. In particular, a scanning electrode for neuroprosthesis applied on muscle of a limb is disclosed.

With regard to a brain spinal interface, US2011/0208265, for example, discloses a multi-programmable trial stimulator for spinal cord, among others. The stimulator can provide a wide range of frequencies, however, a specific selection of frequencies for achieving control of locomotion functions is not disclosed in said document.

US2012/0330391 discloses a method for using spinal cord stimulation to treat symptoms of motor disorders including implanting a stimulation lead within a ventral portion of the epidural space. Frequencies higher than 100 Hz with a pulse width of less than 20 µs are disclosed.

WO2012/094346 discloses a method wherein electrical stimulation is applied to a portion of a spinal cord of a patient with a neurologically derived paralysis. Optionally, the disclosed method can be repeated using electrical stimulation having different sets of parameter values to obtain quantifiable results generated by each repetition of the method. Then, a machine learning method may be executed by at least one computing device. The machine learning method builds a model of a relationship between the electrical stimulation applied to the spinal cord and the quantifiable results generated by activation of the at least one spinal circuit. A new set of parameters may be selected based on the model.

In US2002/0115945 a method for restoring gait in individuals with SCI is disclosed, wherein epidural spinal cord stimulation is combined with partial weight bearing therapy.

In EP2486897, a closed loop brain-machine interface is disclosed, wherein neural signals are acquired and translated into movements performed by a machine. Sensory feedback is also provided. Said interface can be used for restoring voluntary control of locomotion. In the disclosed interface, however, signals are acquired directly from the brain of the subject, motor commands are extracted and movements are effected by an actuator.

In WO2013/071309, transcutaneous electrical spinal cord stimulation (tESCS) is used as a noninvasive method in rehabilitation of spinal pathology. The electrical stimulation is preferably delivered at 5-40 Hz at 20-100 mA. As in WO2012/094346, the possibility of a method and a model of relationship between electrical stimulation and results is disclosed.

WO2007/047852 discloses a method of treating a patient by providing an electromagnetic signal. Closed-loop neuroprosthetic devices are known in the prior art for use, for example, for predicting and preventing epileptic seizures (see for example U.S. Pat. No. 8,374,696 and US2007/0067003).

There is still the need of a method for improving and restoring locomotor functions in subjects with neuromotor impairments, in particular after spinal cord injury.

It is known that EES can be useful for facilitating locomotion in subjects with spinal cord injury and Parkinson's disease.

It is also known that each EES pulse generates a reflex response in the muscle. During stepping, EMG bursts are built from a succession of these reflex responses, which are modulated naturally during the different phases of the gait-cycle, but which may also be directly affected by the parameters of stimulation (namely frequency, amplitude and pulse-width).

There is the need of a real-time control system wherein EES can be modulated, and thus optimized, during the gait-cycle during locomotion, so that a precise control of gait patterns, muscle activity, and foot trajectory can be achieved, and also for accurate upper-limb control (for precise reaching and grasping).

The control and modulation of the electrical stimulation is particularly advantageous for facilitating and improving locomotion functions.

For example, a controlled electrical stimulation helps compensating for the fatigue deriving from an external source of muscle activity. When non-controlled EES-induced locomotion is performed, fatigue yields a decreased flexion and extension pattern during stepping over time thus inducing lower stepping and eventually collapse.

It has now been found that there is a linear relationship between the frequency of electrical stimulation applied in the epidural and subdural space and relevant parameters of gait.

In particular, it has now been found that there is a linear relationship between the frequency of EES and relevant parameters of gait, in particular step height. This relationship has been used for the development of models and control algorithms which allow for a controlled modulation of locomotor patterns through the adaptation of EES frequency, thus achieving real-time control of locomotion.

It has been found that EES frequency clearly and consistently modulates locomotor patterns in subjects with SCI or with lesions of the upper limbs or head in unique and predictive ways.

Gait features that were most correlated with changes in EES frequency can be grouped into functional clusters of flexion, extension, speed and variability along Principal Component Analysis (PC).

In particular, it has been found that the relationship between EES frequency and step height (i.e., the maximum height reached by the foot during each gait cycle) is close to linear and step height is modulated with the frequency, which allowed us to build a linear input-output model, particularly useful for EES control.

It has also been found by the inventors of the present invention that EES applied at lumbar and sacral locations promotes whole-limb flexion and extension, respectively. Also, when EES is applied on the lateral side of the spinal cord the effects of the stimulation are restricted to the limbs on the stimulated side. Real-time algorithms have thus been developed to apply EES to different sites of stimulation, preferably to 4 or more sites based on the actual phase of the gait cycle.

It has further been found that the timing at which stimulation at each site is turned on and off is critical. Each site of EES stimulation modulates a specific functional effect, including facilitation of extension and flexion of the left versus right limbs, based on the actual phase of the locomotor movement.

This rolling burst EES pattern markedly increases the EMG activity of limb muscles, and promotes locomotion with improved interlimb and intralimb coordination, and superior weight-bearing levels compared to continuous EES.

In particular, it has also been found that subdural stimulation promotes coordinated, weight bearing stepping of a paralyzed limb with improved gait characteristics. More in particular, subdural stimulation requires reduced electrical current threshold to be effective and achieves more specific unilateral recruitment of motor neurons.

SUMMARY OF THE INVENTION

An object of the present invention is a closed-loop system for real-time control of epidural and/or subdural electrical spinal cord stimulation characterized in that it comprises
 a. means for applying to a subject a neuromodulation with adjustable stimulation parameters (or values), said means a) being operatively connected with
 b. a real-time monitoring component comprising sensors continuously acquiring feedback signals from said subject, said signals being neural signals and/or signals providing features of motion of said subject, said system b) being operatively connected with
 c. a signal processing device receiving said feedback signals and operating real-time automatic control algorithms, said signal processing device being operatively connected with said means a) and providing said means a) with new stimulation parameters (values), with minimum delay.

In an embodiment of the invention said means a) for neuromodulation comprise an epidural and/or subdural electrical stimulation device.

Indeed, electrical stimulation can be applied in the epidural and/or in the subdural space.

In an embodiment of the invention, said stimulation parameters are waveform, amplitude, pulse width and frequency. Each parameter can be independently adjusted at each cycle.

In a preferred embodiment, said stimulation parameter is frequency.

In a preferred embodiment of the present invention, said means a) can provide a stimulation frequency comprised between 5 and 120 Hz, preferably between 25 and 95 Hz, wherein the resolution is, preferably, of 1 Hz.

In one embodiment of the present invention, said means a) comprises one or more electrodes, preferably an electrode array. Said means a) can also comprise an implantable pulse generator.

Said electrodes can apply the epidural and/or subdural ES (electrical stimulation) to any stimulation site along the spinal cord of the subject. Preferred stimulation sites are lumbar and sacral sites for lower limb stimulation and cervical sites for upper-limb stimulation. Lower limb stimulation is applied, for example, for facilitating standing and walking in a subject; upper-limb stimulation is applied, for example, for facilitating reaching and grasping.

In a preferred embodiment of the invention, said stimulation sites are at least two and each stimulation site can be independently turned on or off.

In an embodiment for facilitating locomotion, the stimulation applied by means a) is phase dependent. This means that specific electrodes are activated during specific sub-phases of the gait cycle. In an exemplary embodiment, the lateral extensor-related (sacral) electrodes are activated during stance, and lateral flexor-related (upper lumbar) electrodes are activated during swing. When is inactive, the amplitude of the corresponding electrodes is zero. Thus in this embodiment, electrodes applied on sacral and lumbar sites are alternatively activated to promote, respectively, whole-limb extension or flexion.

In an alternative embodiment, the stimulation applied by means a) is a burst stimulation.

For burst stimulation it is intended that each electrode is activated for a certain time ("burst"), wherein the activation times of each electrode and the duration of each activation is pre-defined by a user, said user being preferably a clinician or a physiotherapist.

In one embodiment of the present invention stimulation is location-specific, wherein the stimulation parameters of each individual electrode (waveform, amplitude, pulse width, frequency) can be independently modified in real time.

In another embodiment of the present invention stimulation is time-specific (burst stimulation), wherein each single electrode can be individually turned ON and OFF in real time based on external trigger signals.

In an additional embodiment of the present invention stimulation is frequency-dependent.

In an embodiment of the invention, the real-time monitoring component b) is a motion capture system, an accelerometer or a gyroscope.

In another embodiment, said sensors of b) can be selected from the group consisting of: force sensors, electromyographic sensors, joint angle sensors, flow sensors and pressure sensors.

In a preferred embodiment of the present invention, said monitoring component b) is a motion capture system comprising three or more cameras and position markers placed on the subject, preferably on the hindlimb, more preferably on any of one or more crest, hip, knee, ankle and foot and/or on the forelimb, in particular on any of one or more shoulder, elbow, wrist, hand and digits.

In a further embodiment, said feedback signals acquired by the sensors of b) are neural signals.

Neural signals provide information about the subject locomotor state and its motor intention. Preferably, said neural signals are cortical signals. Cortical signals can be recorded, for example, from sensory, motor, sensorimotor or pre-motor cortex. Said signals can be recorded intra-cortically or using Electroencephalography (EEG) systems. Exemplary neural signals which may be recorded are Single-Unit activity, Multi-Unit activity or Local Field Potentials.

Neural signals can be detected by neural probes situated in the cerebral area of interest. Neural probes are preferably electrode arrays implanted in the area of interest. For example, electrodes may be implanted in the limb area of the sensorimotor cortex.

The local field potential (LFP) and multiunit activity (MUA) are extracellularly recorded signals from a local network of neurons.

Therefore, according to the teaching of the present invention said neural signals can provide indirect features of motion of said subject which can be used alone or in combination with signals providing direct features of motion of the subject, as explained in the foregoing description, together composing the feedback signals.

In one embodiment of the present invention, said signal processing device c) operates a program comprising an automatic control algorithm that interfaces simultaneously with the data flow from said real-time monitoring component b) and the means for epidural electrical stimulation a) in real time.

In one embodiment of the present invention for facilitating locomotion, the signal processing device c) acquires feedback signals from said monitoring component b), detects in real-time key events of gait using feature detection algorithms, and automatically adapt stimulation parameters online, thus providing said means a) with new stimulation parameters values.

In another embodiment of the present invention, the signal processing device c) acquires feedback signals from b) providing information on foot kinematics features of the subject and from said signals it detects gait events based on the elevation of the foot in order to detect foot-strike events and toe-off events, preferably from both hindlimbs, and thereby defining specific sub-phases of gait. Preferably, said sub-phases of gait are the stance-phase and the swing-phase.

In this preferred embodiment of the invention, said device c) identifies the stance-phase and the swing-phase within each gait-cycle of locomotion, and provides means a) with new stimulation parameters values. Preferably, means a) comprises several electrodes applied on different stimulation sites, which are turned on or off according to the information provided by device c) so that whole-limb extension is provided during the stance phase and whole-limb flexion is provided during the swing phase.

Another object of the present invention is the above system for use for facilitating locomotor functions in a subject suffering from a neuromotor impairment.

In an embodiment of the present invention, said neuromotor impairment is selected from the group consisting of partial or total paralysis of limbs. Said limb paralysis can be unilateral or bilateral. In particular, said neuromotor impairment is consequent to a spinal cord injury, an ischemic injury resulting from a stroke, a neurodegenerative disease, preferably Parkinson disease.

A further object of the present invention is a system as above defined for restoring voluntary control of locomotion in a subject suffering from a neuromotor impairment further comprising an apparatus selected from the group consisting of at least one of a treadmill or a robot-assisted body-weight support or a multidirectional trunk support system.

It is also an object of the present invention, a method for determining optimal stimulation parameters for a subject suffering from a neuromotor impairment and undergoing a process for facilitating locomotor functions characterized in that it comprises the following steps:

a) determining a first electrical stimulation which has been applied to said subject bearing means for applying an epidural and/or subdural electrical stimulation with adjustable stimulation parameters;

b) acquiring feedback signals from said subject, said signals being neural signals and/or signals providing features of motion of said subject, through a real-time monitoring system, while this first stimulation occurs;

c) transmitting said feedback signals to a signal processing device;

d) calculating by means of said signal processing device operating a Real Time Automatic Control Algorithm new stimulation parameters;

e) providing instructions to said means of step a) for applying a second epidural and/or subdural electrical stimulation so that said means are capable to administer a second electrical stimulation with said new stimulation parameters calculated in step d) to said subject.

The above method can be implemented in a system for real-time control of epidural and/or subdural electrical stimulation.

In one embodiment, in step d) said Real Time Automatic Control Algorithm comprises a feedforward component employing an input-output model which is a single input-single output model (SISO), wherein one stimulation parameter is changed to control one gait feature, or, alternatively a multiple input-multiple output (MIMO) model, wherein multiple stimulation parameters are adjusted to obtain a single desired gait feature (output).

Another object of the present invention is a method for facilitating standing and walking functions in a subject suffering from neuromotor impairment comprising the following steps:
 a) using a system for restoring voluntary control of locomotion comprising the closed-loop system above described;
 b) providing to said subject a first epidural and/or subdural electrical stimulation with adjustable stimulation parameters;
 c) acquiring feedback signals from said subject, said signals being neural signals and/or signals providing features of motion of said subject;
 d) transmitting said feedback signals to a signal processing device;
 e) calculating by means of said signal processing device operating a Real Time Automatic Control Algorithm new electrical stimulation parameters;
 f) providing to said subject a second epidural and/or subdural electrical stimulation with said new electrical stimulation parameters calculated in step e), and optionally
 g) administering to said subject before and/or during administration of said first and/or said second electrical stimulations a pharmaceutical composition comprising at least one agonist to monoaminergic receptors.

In one embodiment, in step e) said Real Time Automatic Control Algorithm comprises a feedforward component employing an input-output model which is a single input-single output model (SISO), wherein one stimulation parameter is changed to control one gait feature, or, alternatively a multiple input-multiple output (MIMO) model, wherein multiple stimulation parameters are adjusted to obtain a single desired gait feature (output).

Another object of the present invention is the system disclosed above for facilitating and/or restoring voluntary control of locomotion in a subject suffering from a neuromotor impairment.

The present invention will be disclosed in detail also by means of Figures and Examples.

FIGURES

Figure 3:
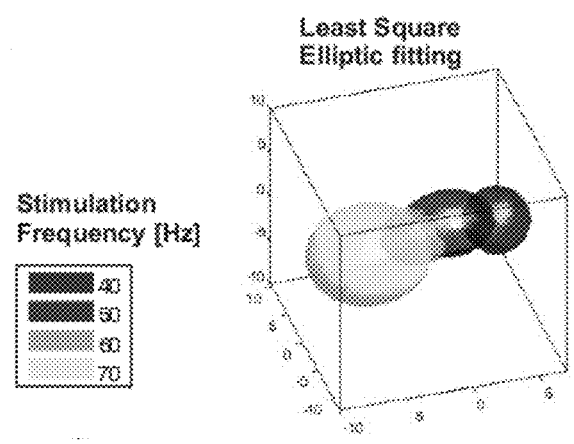

FIG. 3 shows a Statistical Representation of Modulatory Capacities of EES Frequencies in PC space. PC analysis was applied on all gait cycles recorded from all rats (n=5) under different EES frequencies (here ranges from 40 to 70 Hz as shown). Each point in 3D space represents a gait cycle under a given condition once projected in the 3-dimensional PC space. Data points clustered in distinct spatial locations, revealing that different stimulation frequencies modulated locomotor patterns in the same direction in all the rats.

Figure 4:
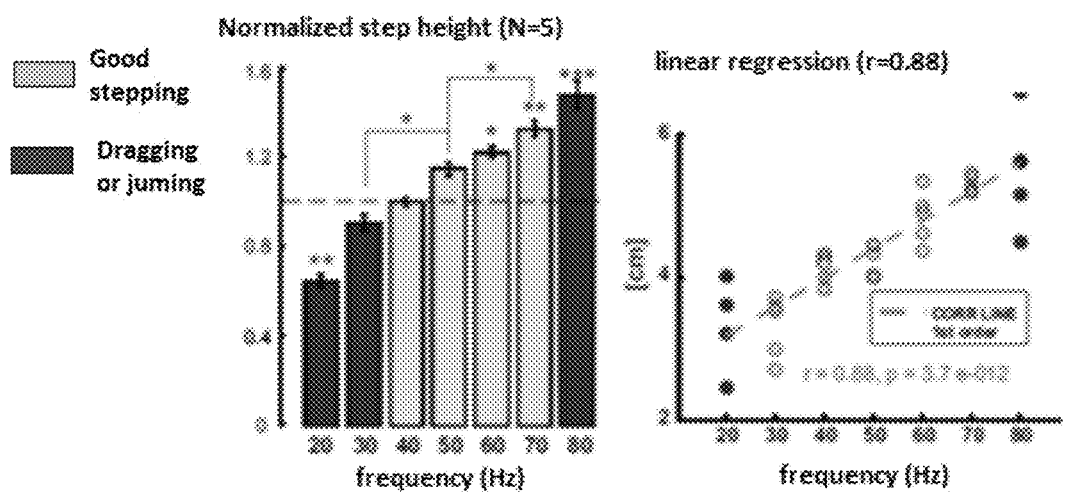

FIG. 4 shows modulation of step-height with frequency of stimulation, and linear regression that may be used as linear input-output relationship.

Figure 5:
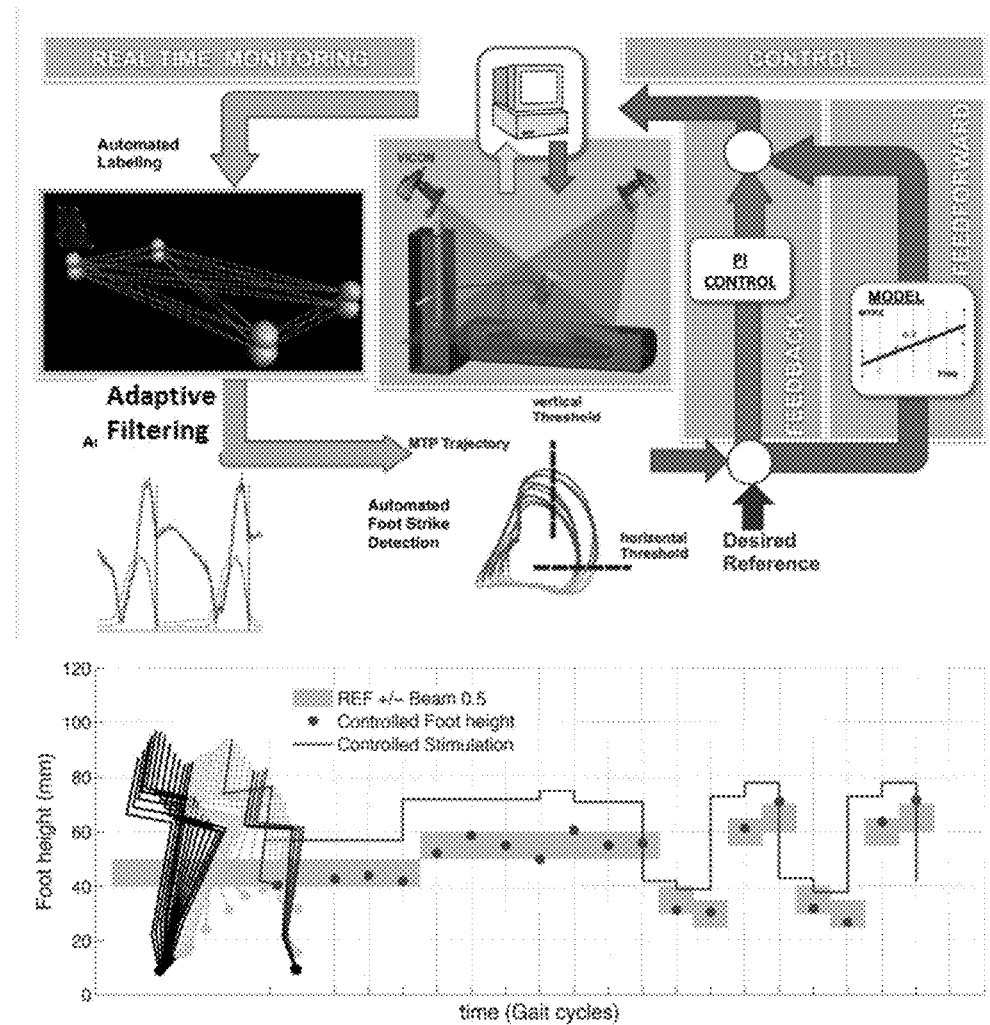

FIG. 5 shows a closed-loop monitoring and control setup. The controller employs the linear model between frequency and step-height, and employs it in conjunction with an error-corrector (PI controller) to adapt the stimulation at each gait cycle. Bottom graph shows the desired reference trajectory and the modulation over time.

Figure 6:
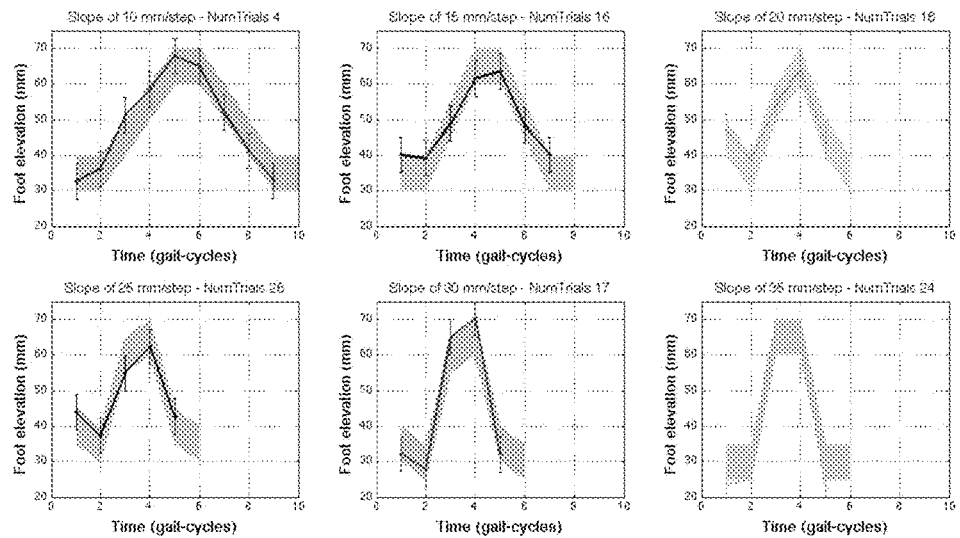

FIG. 6 shows a "Scissor task". The desired ref (shaded area) is constantly changed at every gait cycle, compelling the controller to continuously adapt and use its feedforward component (linear model). Different changing rates were applied, ranging from 11mm/step to 35mm/step (upper limit). Results are consistent for n=4 animals. For all cases, the step-height was accurately positioned.

Figure 7:
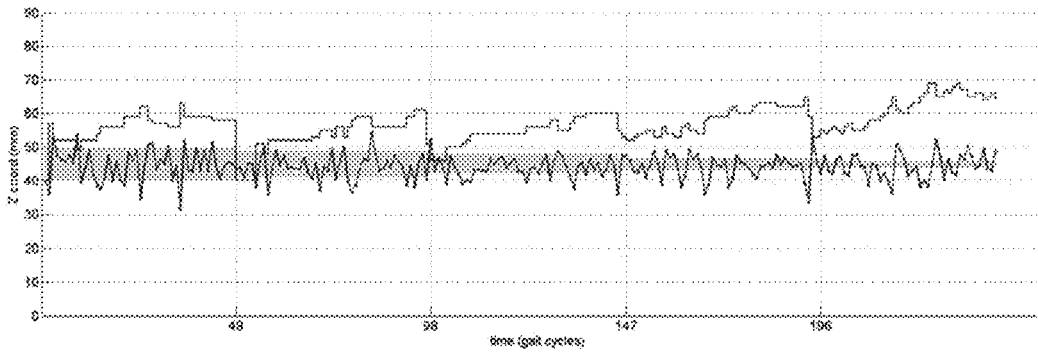

FIG. 7 shows step-heights as the beam (within which errors are not corrected) is reduced from +/−5mm (left) to +/−1mm (right). Even though the control increasingly needs to act to compensate for steps out of the beam, the actual variability remains in similar values.

Figure 8:
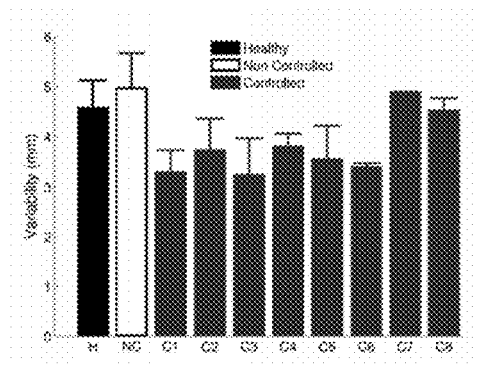

FIG. 8 shows inherent variability in stepping under different conditions: Healthy (black), non-controlled 40Hz stimulation (white) and controlled (grey) with different beams (+/1mm for C1, etc).

Figure 9:
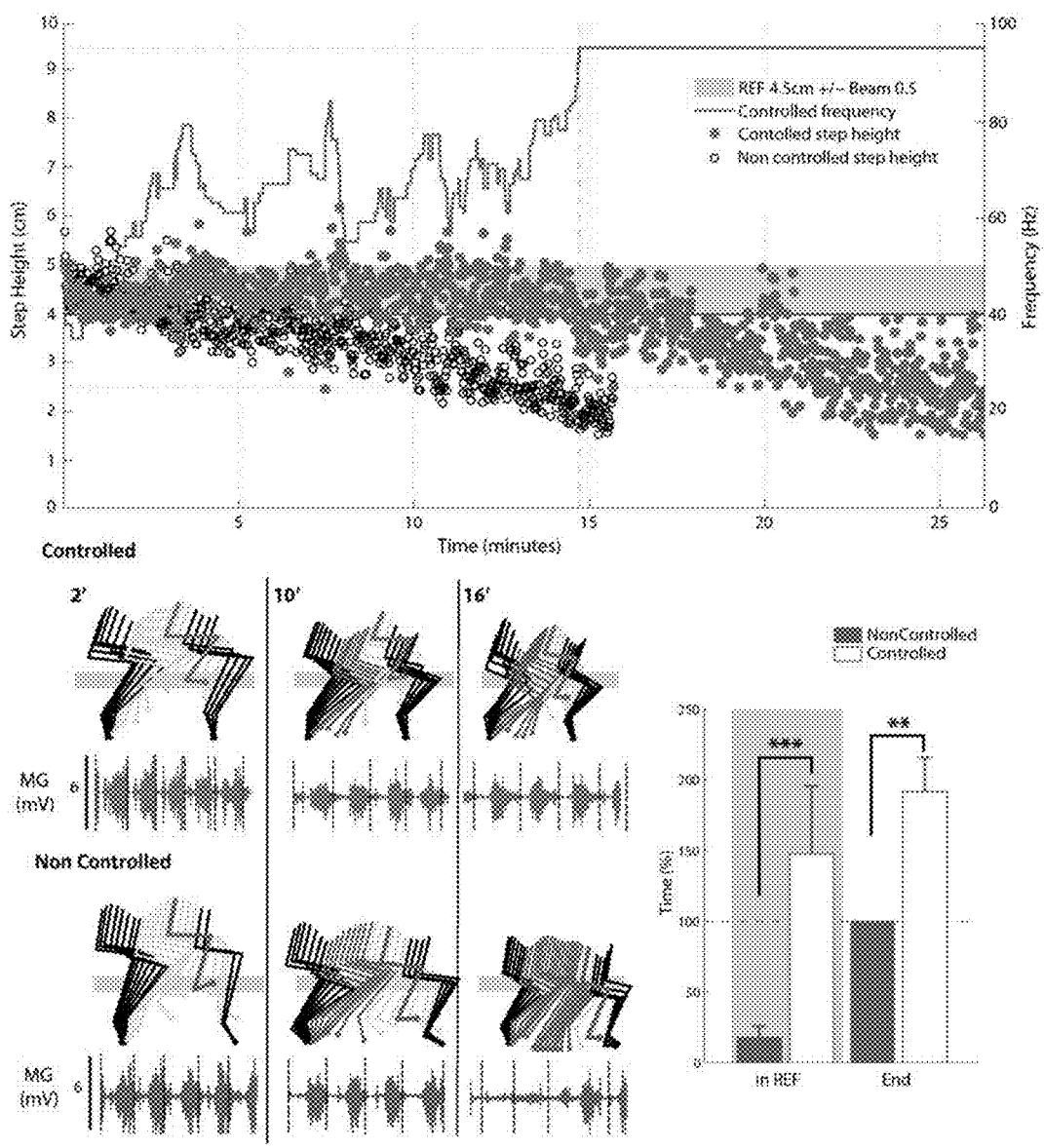

FIG. 9 shows a fatigue experiment & rehab application ( num animals =3). The statistics point out that the controlled output maintains correct stepping (in the desired band) 5 to 6 times longer than in the non controlled case. The full length of the trials are themselves twice as long in the controlled case than in the non-controlled one.

Figure 10:
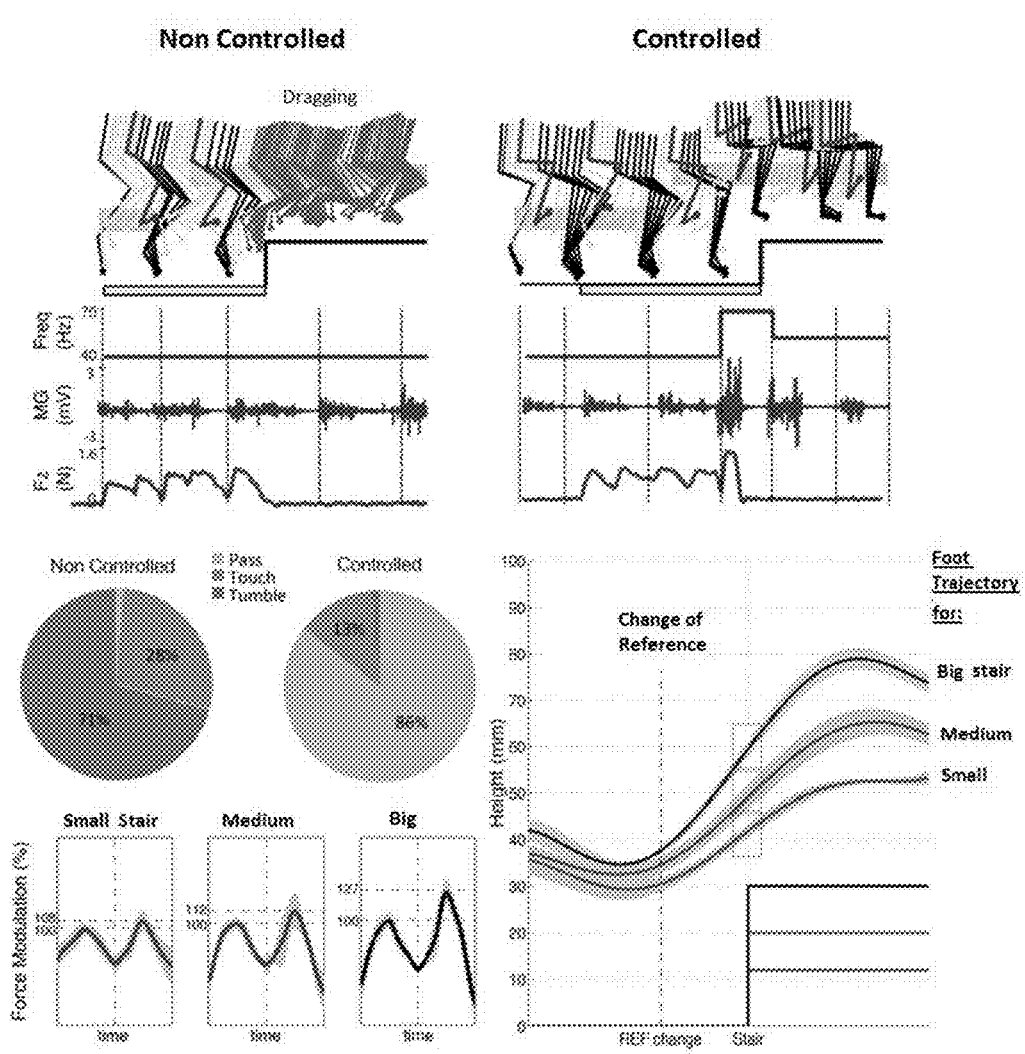

FIG. 10 shows robot trials and stair-climbing application - num animals =4. The statistics of the kinematic trajectories (bottom right −mean +/- sem) clearly show that controlled outputs followed the desired height above the staircase. This also implied an adaptive modulation in force (bottom left) for each condition.

Figure 11:
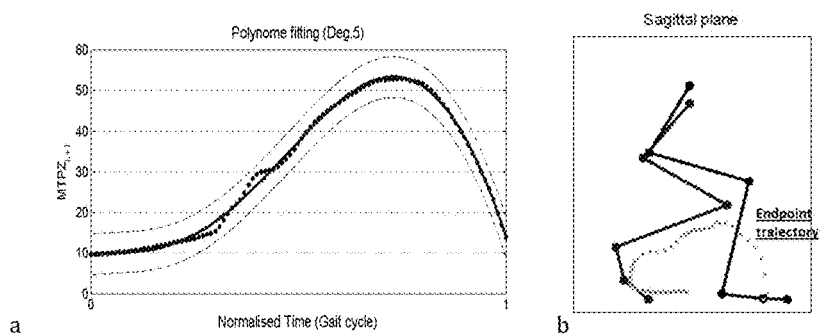

FIG. 11 shows a Left (a): Polynomial parameterization of output foot elevation of the whole gait cycle. This enables to quantify time in a few parameters that expand our output description. Right (b): Body position to account for biomechanics in the input description.

Figure 12:
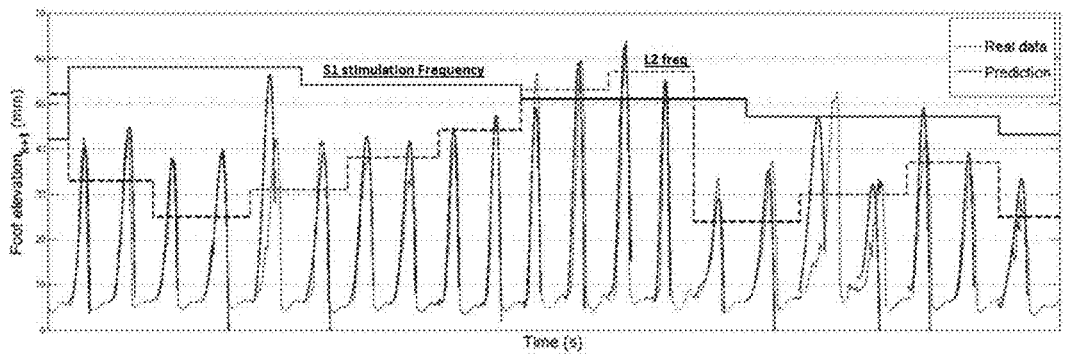

FIG. 12 shows a superposition of model output for each gait-cycle and actual data recorded, as the two electrodes S1 and L2 change independently (black straight and dotted lines).

Figure 13:
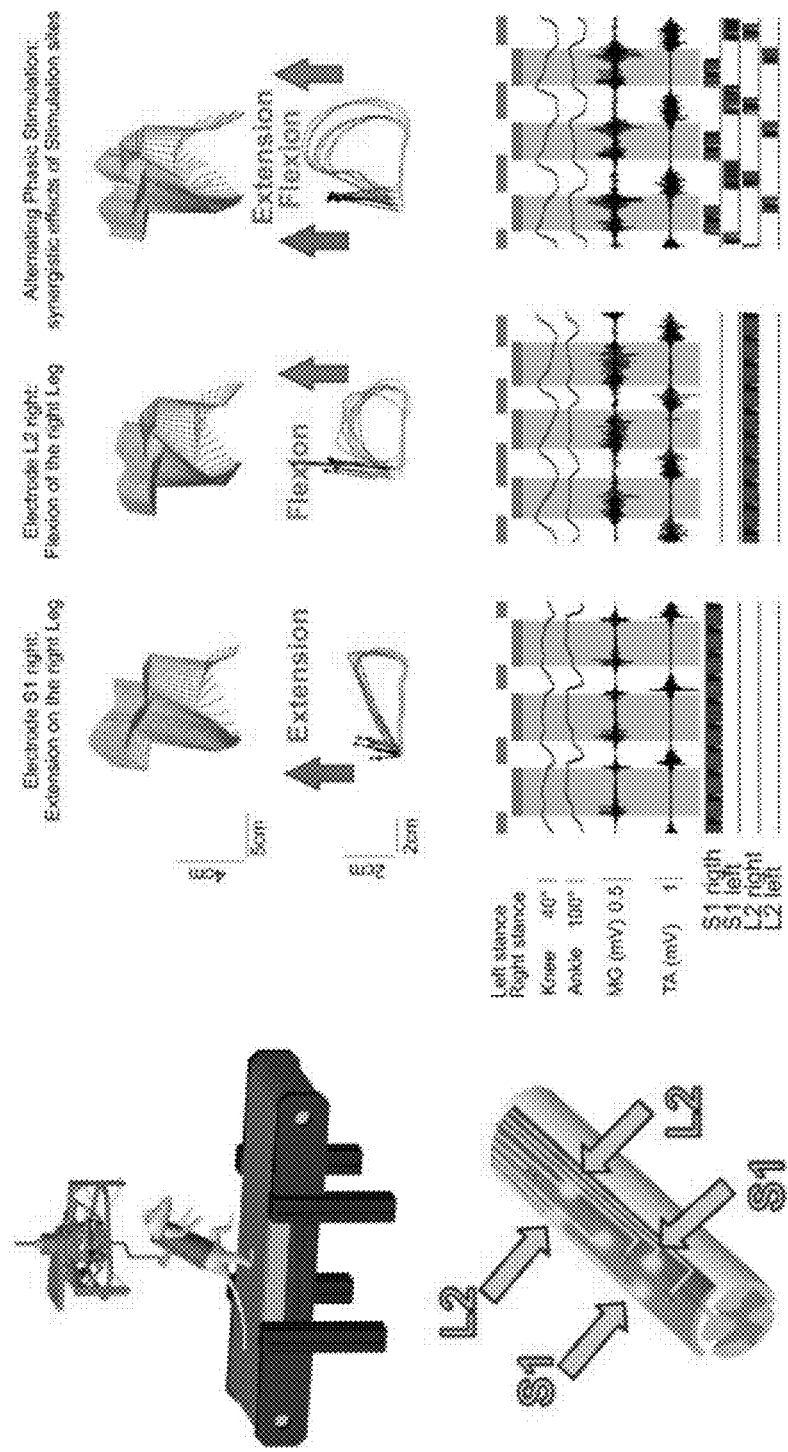

FIG. 13 shows a location-specific stimulation with a multi-electrode array. Stimulation is triggered for each electrode based on the sub-phase of the gait cycle (lateral sacral electrode during stance, lateral lumbar electrodes during swing). This time- and location-dependent stimulation results in enhanced whole-limb extension and increased whole-limb flexion, as observed through kinematic end-point trajectories. The activity of the key muscles responsible for these movements is increased manifold.

Figure 14:
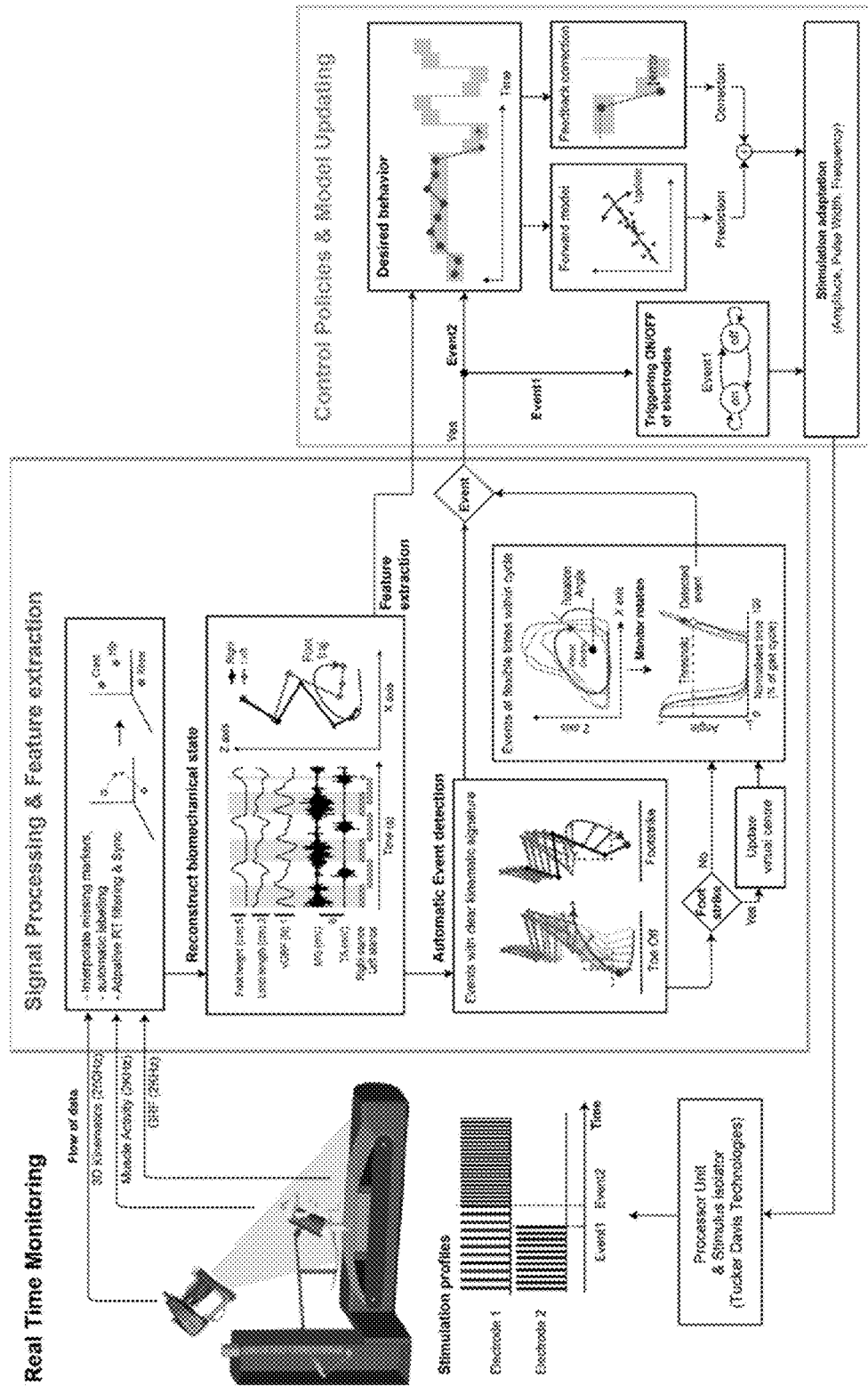

FIG. 14 shows a scheme of an embodiment of the invention, illustrated in the case of rehabilitation of rodents on a treadmill. The subject is continuously monitored in real time (in this case, kinematics recorded using reflective markers attached to landmark joints, tracked using motion capture cameras operating at 200Hz - Electromyographic and Ground Reaction Forces recorded at 2kHz). All the information is synchronized, all signals are filtered in real time using adaptive filters, and kinematics interpolated to deal with missing markers (e.g., due to occlusions). Once the biomechanic state of the system is complete, the closed loop system proceeds to (i) automatically detect key gait events and (ii) extract meaningful features for control. Two types of gait events are detected using complementary online algorithms. These include events that have a clear kinematic signature (e.g., foot strike and toe off, for which simple kinematic thresholding is accurate enough) but also user-defined moments within the gait cycle (e.g., middle of swing). Custom made algorithms monitor the rotation of the foot around a virtual centre and detected events through threshold-crossing in angle space. These events trigger the control calculations, which can either turn ON or OFF individual electrodes (case of event 1, which triggers OFF electrode 2) for phasic stimulation, or start feedback-feedforward control to achieve a desired behavior (case of event 2, which calculates the appropriate frequency correction applied to electrode 1).

Figure 15:
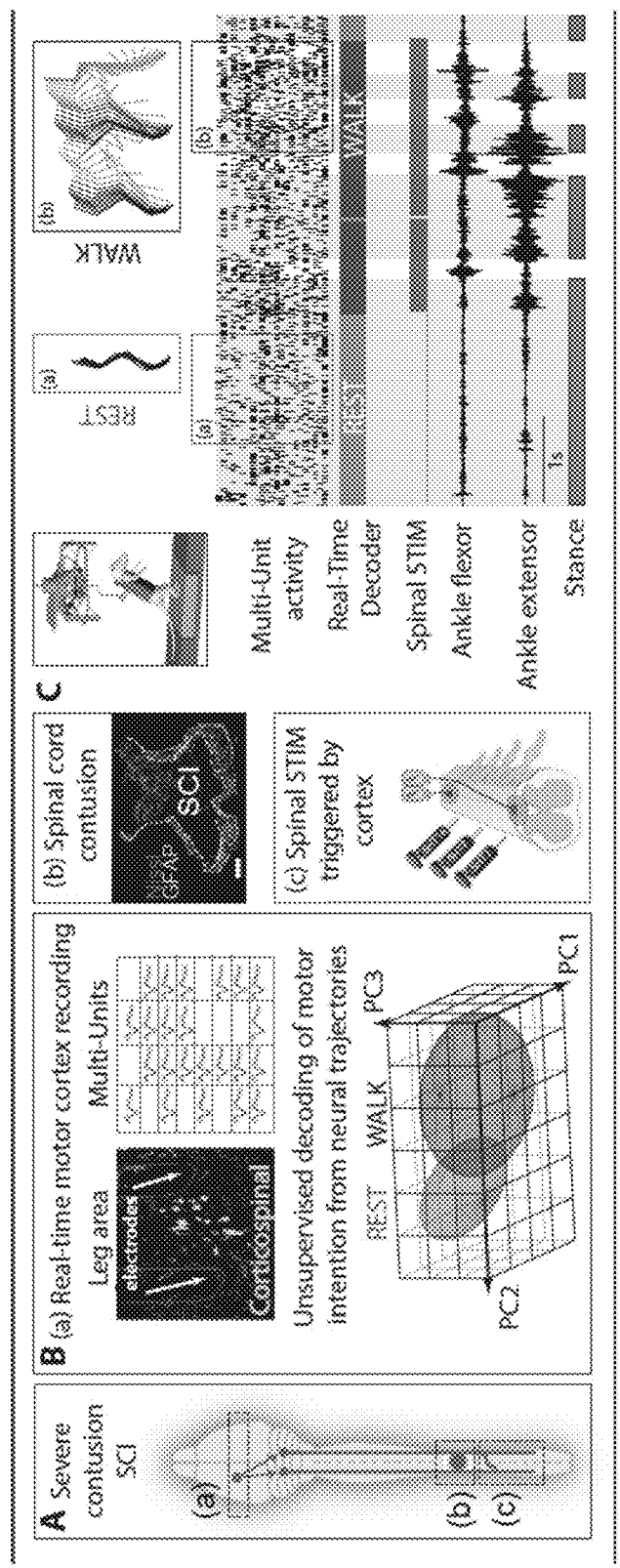

FIG. 15 shows a scheme of an embodiment of the invention wherein the voluntary walking intention of the subject is detected from cortical recordings and the electrical stimulation is provided below the injury level. A) A severe contusion interrupts most of the fibers connecting the motor cortex and the segments of the spinal cord where motoneurons controlling hindlimb locomotion are located. B) a) Micro-wire electrode arrays inserted in the leg area of the rats' motor cortex record multi-unit neuronal activity that is decoded in real-time into discriminating 'idle' or 'walk' behavioral states. b) A severe spinal contusion spares few fibres travelling across the injury (GFAP =glial fibrillary acidic proteins, NISSL =nucleic acid staining), c) thus the neural drive is replaced by pharmacological and electrical intervention at the sublesional spinal level. C) On overground tests the decoder is able to capture the cortical multi-unit activity and detect the subject animal's intention to walk. It consequently delivers temporized stimulation through the spinal electrodes, with high precision in the synchronization to the onset of locomotion.

Figure 16:
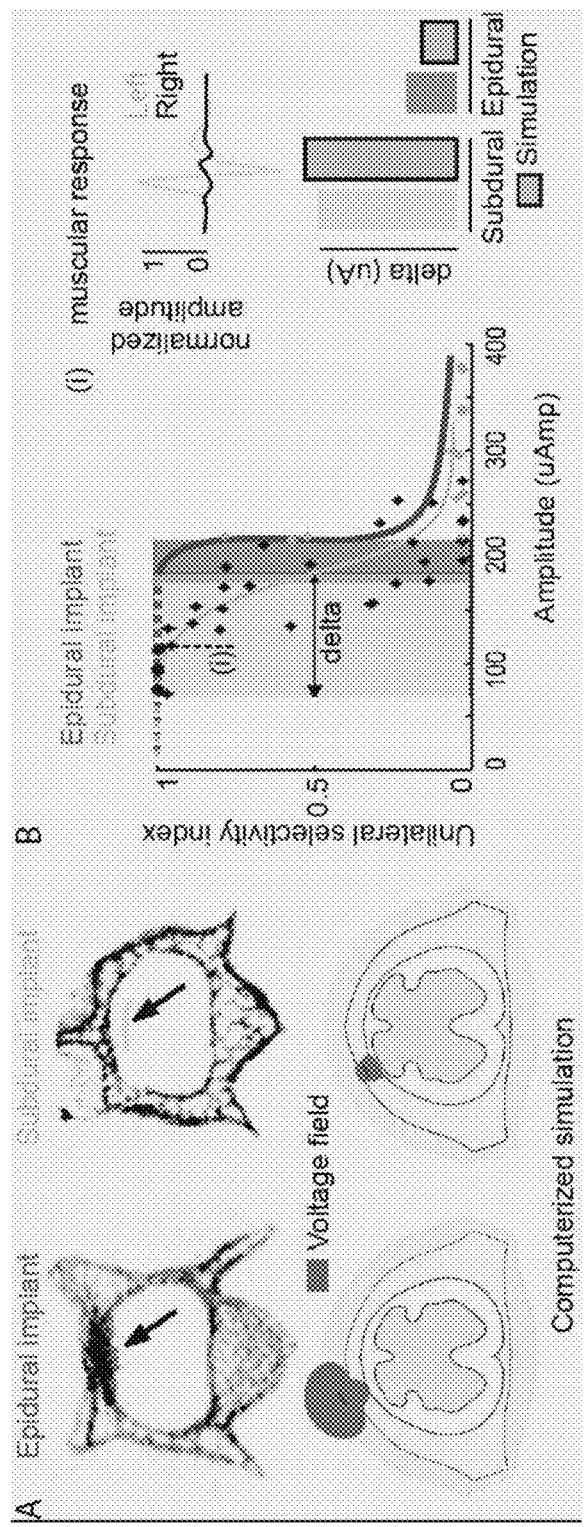

FIG. 16 shows a comparison between epidural (dark grey) and subdural (light grey) electrical stimulation. (A) Top: Computerized Tomography (CT) Scan of epidural and subdural implants. Bottom: computerized simulation show increased selectivity of unilateral voltage fields for subdural implantation indicated by the more restricted voltage field (red area in diagram). (B) Electrophysiological experiments confirmed that subdural stimulation required reduced current threshold, and achieved more specific unilateral recruitment of motor neurons compared to epidural stimulation. Unilateral selectivity was calculated as 1 —ipsilateral muscle recruitment/contralateral muscle recruitment. The graph shows that subdural stimulation achieved an increased amplitude range (delta) for unilateral muscle recruitment.

Figure 17:
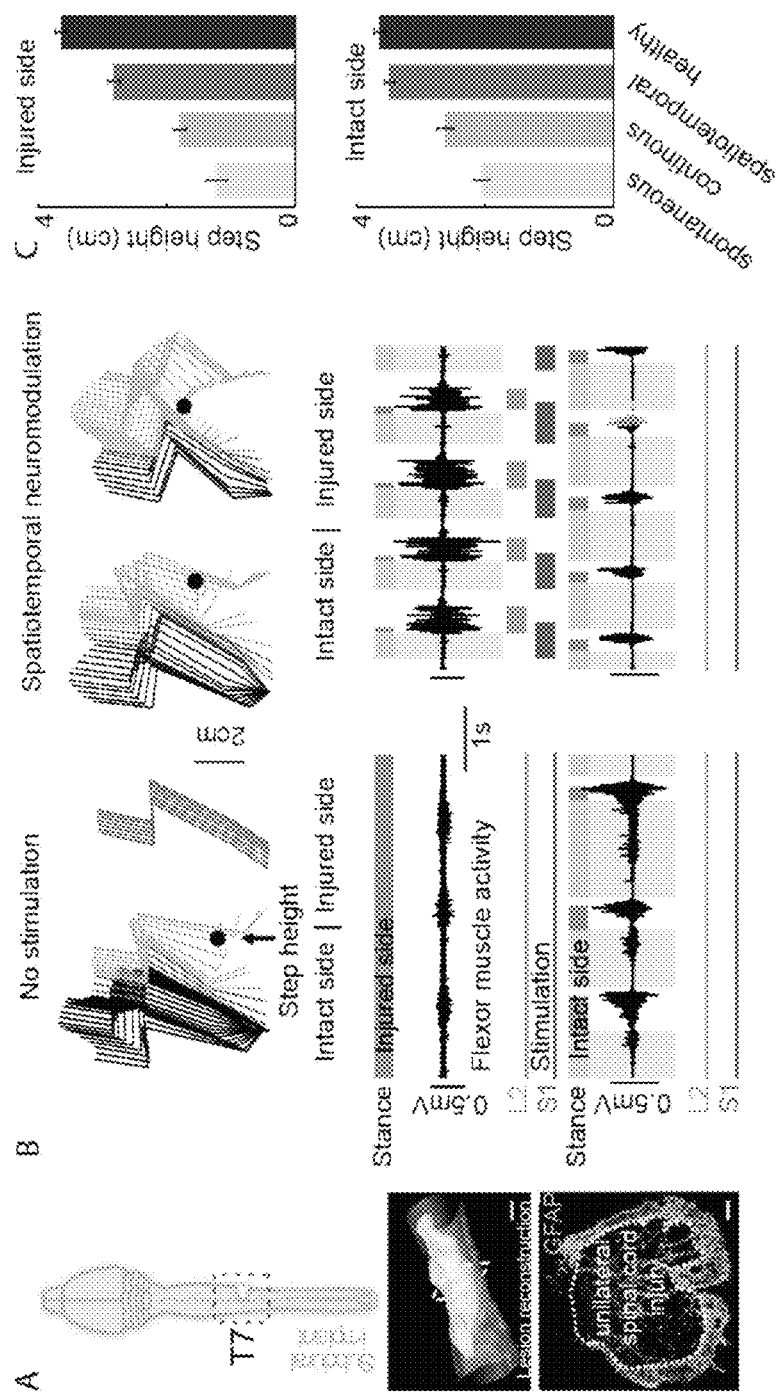

FIG. 17 shows a closed loop multisite spinal cord stimulation applied through subdural electrodes improves stepping capacities after unilateral spinal cord injury. (A) Anatomical reconstruction of a unilateral spinal cord injury leading to unilateral hindlimb impairment. (B) Subdural spinal cord stimulation delivered through the lateral electrodes (electrode promoting limb flexion: Flex, electrode promoting limb extension: Ext) of a soft subdural implant (40Hz, 0.2ms, 20-50µA) promoted coordinated, weight bearing plantar stepping of the paralyzed hindlimb with improved gait characteristics compared to continuous stimulation. (C) Quantitative comparison of step height in rats with unilateral spinal cord injury and healthy animals. Closed loop multisite spinal cord stimulation (Closed loop) improves step height compared to continuous open loop stimulation (Continuous).

DETAILED DESCRIPTION OF THE INVENTION

Within the frame of the present invention, the following definitions are provided.

"Device": means a single device, also intended as "means" or "component", namely a device which, taken alone performs a defined function. Examples of devices are an epidural electrical stimulator (EES), a sensor, a signal processor.

"Apparatus": means a component comprising one or more devices cooperating to provide a more complex function. Examples of apparatuses are a computer, a monitoring component. An apparatus can also be integrated in a system.

"System": means an ensemble of one or more apparatuses and/or devices cooperating to provide an even more complex function. Example of system is the closed-loop system of the present invention.

"Gait cycle": defines, during locomotion, the motions from initial placement of the supporting heel of a subject on the ground to when the same heel contacts the ground for a second time.

"Input-output Feedforward component": means a component within a control system which is employed to predict the outcome of an input. In the present invention, it captures the relationship between EES and locomotor patterns and is employed to predict the outcome of the applied stimulation.

"Feedback component": means a component that corrects errors observed between the desired output and the obtained output. Within the frame of the present invention, this component complements the feedforward model in the control structure. The feedback component corrects for errors observed between the desired locomotor pattern and the behavior observed.

"Feedback signals": means signals from the subject which can be signals providing direct features of motion, such as for example (i) gait events, in particular foot-strike and foot-off events, (ii) specific activation of muscles or forces, or indirect features of motion such as subject locomotor state and its motor intention; these latter signals are neural signals originating for example from brain cortex, in particular sensory, motor or pre-motor cortex.

"Proportional Integral control": means a type of feedback algorithm that generates a correction that is proportional to the error and to the integral (cumulated over time) of the error. "Principal Component analysis": means a dimensionality reduction algorithm that helps analyzing data in a subspace, where the dimensions that carry most of the variance are maintained.

"Operatively connected" means a connection capable of carrying data flow between two or more input and/or output data ports. The connection can be of any suitable type, a wired or a wireless connection.

"Signal processing device": means any device capable of elaborating input signals and produce output signals. Said device can be a processor, incorporated in a more complex apparatus or system, such as for example a computer. According to the present invention, said signal processing device allows calculating electrical stimulation parameters, stimulation sites, and time of stimulation, to be used with the means for applying an epidural electrical stimulation.

A locomotion feature, or gait feature, is a kinematic parameter characterizing the gait cycle.

For "facilitating standing and walking" is intended an increase of the movements magnitudes of the hind limb joints as well as an improvement of locomotor stability. In particular, the step height and flexor muscle activity are improved and the limb dragging is reduced. Also, a better coordination of extensor and flexor activity (reciprocal) and full body weight support is achieved.

The present invention will be now disclosed in detail referring to the exemplary embodiment of facilitating and restoring locomotion, with particular reference to lower limbs, being intended that the teaching of the invention is applicable to every kind of neuromotor impairments, such as, for example, impairment of upper limbs, head and trunk.

An exemplary representation of the system of the invention is represented in FIG. 14 and herein explained. The subject to which epidural and/or subdural electrical stimulation is applied is continuously monitored in real time. All the information are synchronized, all signals are filtered in real time using adaptive filters, and kinematics interpolated to deal with missing markers (e.g., due to occlusions). Once the biomechanic state of the system is complete, the closed loop system proceeds to (i) automatically detect key gait events and (ii) extract meaningful features for control. Two types of gait events are detected using complementary online algorithms. These include events that have a clear kinematic signature (e.g., foot strike and toe off, for which simple kinematic thresholding is accurate enough) but also user-defined moments within the gait cycle (e.g., middle of swing). Custom made algorithms monitor the rotation of the foot around a virtual centre and detected events through threshold-crossing in angle space. These events trigger the control calculations, which can either turn ON or OFF individual electrodes for phasic stimulation, or start feedback-feedforward control to achieve a desired behavior.

For the purpose of the present invention, the means for applying to a subject an epidural and/or subdural electrical stimulation with an adjustable stimulation frequency, are conventional ones. Commercially available devices for ES and/or EES, as well as custom-designed devices are suitable for carrying out the present invention. In a preferred embodiment, said means for applying an epidural and/or subdural electrical stimulation is a custom-designed device comprising multiple electrodes, named multi-electrode array (MEA), which is particularly useful for site-specific stimulation.

Conveniently, the means for applying an electrical stimulation to a subject can be one or more electrodes, preferably it is an electrode array. Said means can also comprise an implantable pulse generator.

The electrical stimulation is applied to the epidural space and/or to the subdural space of the vertebral column.

The electrical stimulation can be applied to any portion of the spinal cord of a subject. In an embodiment electrical stimulation may be applied by an electrode array that is implanted epidurally in the spinal cord of the subject. Such an electrode array may be positioned at least one of a lumbosacral region, a cervical region, and a thoracic region of the spinal cord. The specific site of stimulation can be chosen by the skilled in the art according to the desired effect. For example, in a preferred embodiment the electrode array is positioned at the lumbosacral region for control of locomotion of lower extremities.

The real-time monitoring component b) comprises sensors continuously acquiring feedback signals from the subject. The acquired signals are neural signals and/or signals providing features of motion of the subject as defined above.

In an embodiment, the real-time monitoring component b) detects the movements of the subject after electrical stimulation has been applied. It can be a motion capture system or an accelerometer or any other equivalent means. In a preferred embodiment, the real-time monitoring component is a motion capture system which comprises limb position markers. These markers are placed on the subject's limb(s) which is (are) stimulated by means a) and are visible by the real-time monitoring component in a way that it acquires 3D coordinates of the limb movement when stimulation by means a) is applied. Typically, markers are of reflective type, reflective type meaning that they reflect infrared light emitted by the cameras thus allowing their tracking, but other types can be used. Examples of other markers suitable for the present invention are optical systems, electromagnetic systems, ultrasonic systems, and combinations of systems suitably integrated by what is known as the "sensor fusion" method, a triangulation system using radio frequency antennae and inertial sensor. The marker positions of the subject are acquired in real-time and associated to specific labels (labels may be for example Crest, Hip, Knee, Ankle, Foot) according to user-defined kinematic model, built on a per-animal basis for high accuracy tracking. Said model evaluates a set of rules that compares X, Y and Z coordinates of each marker, and derives which set of coordinates corresponds to which label. Said kinematic model thus matches 3D positions of markers with the joint they are attached to. Marker positions can be, for example, crest, hip, knee, ankle and foot.

Said set of rules operates in three steps: in a first step it evaluates the mediolateral coordinates of the markers to distinguish between those related to the right and to the left limb, thus identifying two subsets. In a second step, for each one of these two subsets, top-down rules distinguish using the vertical coordinates: crest (highest marker), the couple hip/knee (lower than Crest) and the couple Ankle/foot (lowest two markers). Finally (third step), for each one of these two couples, forward coordinates help distinguish knee from hip (knee is more forward than hip) and foot from ankle (foot is more forward than ankle).

For example, a Vicon Kinematic System (Nexus) can be used as a real-time monitoring component. Other commercially available or custom-built systems are suitable for the present invention.

The acquired coordinates are then transmitted to an external signal processing device (c).

In another embodiment, the real-time monitoring component b) acquires neural signals from the subject as feedback signals. Said neural signals provide information about the locomotor state and the neuronal activity of the subject and transmit them to the processing device c).

Neural signals provide information related to the gait cycle and can be used to control or refine in real time the triggering of electrodes, respectively substituting or co-operating with the kinematic-feedback algorithms described above.

In an exemplary embodiment, electrode arrays implanted in the limb area of the sensorimotor cortex of a subject collect information about the subject locomotor intention. Using machine-learning approaches this information can be decoded and discriminated into two behavioral states, "rest" or "walk". The decoding is then transmitted to the processing device and switches ON or OFF the feedback-feedforward controller, so that the desired locomotor pattern is achieved.

With regard to machine-learning approach, reference can be made to the review "Corticospinal neuroprostheses to restore locomotion after spinal cord injury." D. Borton, M. Bonizzato, J. Beauparlant, J. Digiovanna, E. M. Moraud, N. Wenger, P. Musienko, I. R. Minev, S. P. Lacour, J. d. R. Millán, S. Micera and G. Courtine published in Neuroscience Research, vol. 78, p. 21-29, 2014.

On the external signal processing device c) a program comprising an automatic control algorithm interfaces simultaneously with the Kinematic Data Stream and/or with the Neural Data Stream, i.e. the data flow from the real-time monitoring component b), and the means a). The program and the algorithm can be in any programming language able to operate in real time; for example, it can be in C, C++, C#, Simulink/xPC. Preferably, it is in C++. It can be compiled according to the general knowledge of the skilled in the art using custom-made or commercially available software, for example TDT. Said program is programmed to detect footstrike in real time and to adapt the electrical stimulation at each gait-cycle thanks to the controller part.

In particular, the Neural Data Stream is the data flow from the real-time neural signal monitoring component, while the Kinematic Data Stream is the data flow from the real-time monitoring component detecting the movements of the subject.

In an embodiment of the invention, the program contains three parallel threads. One thread acquires epidural stimulation parameters specified through a graphic user interface in a programming language, for example in C++. The second thread contains a loop which continuously updates the information about marker positions in space. In the third thread, the controller is implemented. In an exemplary embodiment of the invention, the program on the signal processing device works as follows. Once stance detection occurs, a trigger is sent to the program code via, for example, an ActiveX interface. Inside the bioamp processor runs a real time cycle based program at a selected frequency, preferably 24 kHz cycle frequency. The program continuously evaluates the occurrence of an external trigger and then transforms it to an epidural stimulation signal. For this purpose, stimulation parameters from the C++ graphic user interface are acquired by the program code. Once the stimulation signal is generated, it is transmitted to an external stimulus isolator. The stimulus isolator generates the current pulse from an attached battery, for example a 24V, high voltage battery. The current pulse is then transmitted back to the epidural space of the animal at selected stimulation sites through a hardwired connection.

The controller part (herein referred to also as "controller") allows deriving, at each gait-cycle, the optimal ES and/or EES frequency on the basis of the desired locomotion feature output (herein also named reference output). The reference output is entered by the operator (e.g., clinician) based on the desired behavior. The controller will then tune automatically the stimulation to make sure the observed behavior matches the reference thanks to the feedforward component, and adapt said frequency at each gait-cycle on the base of the obtained output, thanks to the feedback component.

The reference output is defined and entered by the operator of the device, for example a clinician, on the base of the desired locomotion pattern. The controller then tunes automatically the electrical stimulation in order to obtain a locomotor pattern matching the reference output.

The controller comprises a feedforward component and a feedback component.

The feedforward component is an input-output linear model, which allows to directly derive the most suited electrical stimulation frequency given the desired reference output at each gait-cycle and to minimize control delays.

Said reference output is a locomotion feature (herein also named gait feature), preferably it is the step height, i.e. the maximum height reached by the foot during each gait cycle.

The input-output model captures the observed relationships between stimulation and gait features. They can then be used to predict and automatically tune stimulation so as to modulate output behavior.

Said model is constantly updated using adaptive fitting algorithms which take into account fatigue and time-varying characteristics of the locomotor system of the subject. Adaptive fitting algorithms suitable for the present invention are known in the art and can be chosen by the skilled in the art according to its general knowledge. An example of this kind of algorithm is the Least Mean Squares (LMS), but other methods for linear or non-linear regression are equally valid.

In the device of the invention, the stimulation frequency applicable by means a) is comprised between 5 and 120 Hz, preferably it is comprised between 25 and 95 Hz.

Pulse-width is kept constant at a value comprised between 0.1 and 1.0 ms, preferably at 0.2 ms. Amplitude is set between 100-300 uA. Actual ranges and sub-ranges can vary from subject to subject.

The feedback component (a Proportional Integral (PI) Control part) of the controller compensates for modeling errors or unexpected disturbances. At each gait-cycle, it calculates the "error" value between the measured output and the desired reference output. On the basis of the calculated error value, it adjusts the input so as to minimize said error. For example, at the end of a foot strike, the maximum step height is determined and the error with respect to the desired reference step height is evaluated; then, the new stimulation frequency is derived.

The new stimulation frequency is calculated by the feedback component according to the following formula 1:

$$F = K_p e + K_I \Sigma_{k=0:t} e_k \quad (1)$$

Formula 1: Sum of Proportional and Integral Correction of the PI Controller

Wherein e is the error, $K_p$ is the proportional term and $K_I$ is the integral term and F is the calculated stimulation frequency.

Interestingly, this type of controller requires little a priori knowledge of the system dynamics, and only employs a reduced number of parameters to be tuned (namely, the proportional term $K_p$ and the integral $K_I$ terms). These are adjusted empirically to match experimental recordings for the subject using the system. The first term is proportional term, which drives the correction in proportion to the error. The second term is proportional to both the magnitude and the duration of accumulated errors, and reduces offsets not taken accounted for by the proportional term. The new stimulation frequencies are determined as the sum of a partial correction plus an integral correction.

Proportional Integral (PI) controllers are the widest and better know types of controllers for any application (they account for 95% of controllers) therefore they belong to the general knowledge and do not require further explanations.

In an embodiment of the invention, the feedforward component of the controller employs an input-output model which is a single input-single output model (SISO), wherein one stimulation feature is changed to control one gait feature.

In said embodiment, stimulation frequency applied at a single electrode or simultaneously in different body sites is the single feature (input) which is changed. The selection of the body site, application mode and positioning of the device depend on the amount of specificity desired and the amount of available electrodes and this can be made by the skilled person.

The body site(s) where the stimulation is applied can vary according to the desired specificity. In a preferred embodiment, stimulation is applied using a multielectrode array (MEA) covering the spinal segments from T12 to S2 if one wants to control and promote leg movements, and/or covering the spinal segments from C3 to T2 if one wants to control and promote arm movements.

In this embodiment using the SISO model, when stimulation is applied on different sites, the stimulation parameters, in particular the frequency of stimulation, are changed simultaneously in all the sites. For example, if electrical stimulation is applied to S1 (sacral 1) and L2 (lumbar 2) sites, frequency of stimulation, and timing of stimulation change together in both sites.

In this embodiment, the single output is a locomotion feature. Said locomotion feature can be, for example, step height, amount of dragging, amount of extension, maximum ground reaction forces. Preferably, it is step height.

In an alternative embodiment of the invention, the system of the invention employs as input-output model, a multiple input-single output (MISO) model, wherein multiple stimulation features are controlled to obtain a single desired gait feature (output).

In said embodiment, the single output is the trajectory of the subject foot height over time. Said trajectory is parameterized by the following formula 2:

$$y(t) = \sum_{i=0}^{5} w_i t^i + \epsilon, t \in [0, 1] \quad (2)$$
$$\equiv [w_0, \ldots w_5], t \in [0, 1]$$

wherein y is the trajectory,
t is the time during which the trajectory is achieved,
$w_i$ wherein i is comprised between 1 and any desired degree of polynomial fitting. In the exemplary formula a polynomial fit of degree 5 is chosen to have a certain degree of accuracy, and ε is the error.

Said multiple inputs are preferably stimulation frequencies applied on different body sites.

Given the effect that biomechanics play on stepping, input description (i.e. the overall information provided as input) can be also increased to account for body position (kinematics) and kinetics. This means that the input is increased by considering as inputs not just stimulation values, but also the biomechanical characteristics of the body. The model is thus implemented by accounting for angular positions and speeds of limb joint angles, preferably the three joint angles in each leg (Hip, Knee and Ankle), along with Ground Reaction Forces (i.e. the maximum forces applied by the body on the ground), and employing said data at each gait-cycle to derive the most suitable stimulation given the current biomechanical state. If desired, other body points can be added or considered, such as for example tips of the feet or any other body point useful to provide more information on the biomechanical characteristics of the body.

Thanks to the use of the MISO model, at each foot strike the best stimulation strategy can be derived for each input, i.e. for each electrode applied in a different body site, so as to generate the desired foot trajectory (output).

In a preferred embodiment, the real-time monitoring system b) provided above, acquires 3D coordinates of a limb of said subject. Conventional, commercially available or custom-designed systems are suitable for the present invention. A motion capture system b) can be, for example, a gyrometer attached to a foot of a subject or a foot-strike detector, for example a force-based switch.

In a preferred embodiment, said means a) for applying to a subject an epidural and/or subdural electrical stimulation with adjustable stimulation parameters values, as above, is an implantable pulse generator, which can be connected to different sites of the spinal cord of a subject. It is able to change stimulation parameters, in particular stimulation frequency, and turn off and turn on different stimulation sites. For example, it can be connected to sacral and lumbar stimulation sites and said sites can be alternatively turned on and off during stance and swing, according to the desired output.

In a preferred embodiment, the stimulation applied for locomotion by means a) is phase dependent. This means that specific electrodes are activated during specific sub-phases of the gait cycle. In an exemplary embodiment, the lateral extensor-related (sacral) electrodes are activated during stance, and lateral flexor-related (upper lumbar) electrodes are activated during swing. When inactive, the amplitude of the corresponding electrodes is zero.

Triggering of each electrode can be based on automatic detection of gait events, derived by the signal processing device c) using feature detection algorithms that use external feedback signals (b). Such algorithms allow to detect gait events such as foot-strike or toe-off. Through this algorithm the processor c) provides means a), with information regarding the turning on or off of specific electrodes, in order to promote whole limb flexion and whole limb extension to increase muscle activity of relevant muscles and thus to improve the locomotor output.

The suitable triggering times are obtained for each electrode through feature detection algorithms monitoring foot kinematics and deriving optimal gait events based on the timing within the gait cycle as defined both by kinematic states and muscular activation.

In a preferred embodiment for locomotion, sacral electrodes are activated (turned on) at footstrike and turned off after the beginning of swing (i.e. after the activation of the tibialis anterior muscle) while lumbar electrodes are activated before the beginning of swing (i.e. before activation of the tibialis anterior muscle) and turned off before foot-strike. This delay is related to the information processing time in the spinal cord, and transfer of the activating neural command through motor nerves to muscles.

In an alternative embodiment, the stimulation applied by means a) is a burst stimulation.

For burst stimulation it is intended that each electrode is activated for a certain time ("burst"), wherein the activation times of each electrode and the duration of each activation is pre-defined by a user, said user being preferably a clinician or a physiotherapist.

In an embodiment of the present invention, and referring to FIG. 13, it is advantageous to provide location-specific stimulation with a multi-electrode array. According to this embodiment, stimulation is triggered for each electrode based on the sub-phase of the gait cycle (lateral sacral electrode during stance, lateral lumbar electrodes during swing). This time- and location-dependent stimulation results in enhanced whole-limb extension and increased whole-limb flexion, as observed through kinematic endpoint trajectories. The activity of the key muscles responsible for these movements is increased manifold.

The closed-loop control system object of the invention can be used for facilitating locomotor functions in a subject suffering from injured locomotor system, especially due to neuromotor impairment, in particular in a subject suffering from partial or total paralysis of limbs.

Therefore, it is an object of the invention the use of said system for facilitating locomotor functions in a subject suffering from a neuromotor impairment.

In particular, said neuromotor impairment can be partial or total paralysis of limbs.

Said neuromotor impairment may have been caused by a spinal cord injury, Parkinson's disease (PD), an ischemic injury resulting from a stroke, or a neuromotor disease as, for example, Amyotrophic Lateral Sclerosis (ALS) or Multiple Sclerosis (MS).

Preferably, the device is used for facilitating locomotor functions in a subject after spinal cord injury, Parkinson's disease (PD) or stroke.

In particular, the use of the device of the invention allows the maintenance over time of stepping heights, thus reducing the fatigue of the subject.

Another advantage of the use of the system of the invention is the improvement of consistency of walking in a subject with a neuromotor impairment, wherein for consistency of walking is intended the amount of repeatable steps with similar locomotor features performed by the subject.

In a particular application, the system of the invention is used to help the subject in overcoming an obstacle. For example, it is used for helping the subject in climbing stairs. In this application, the desired output in the system is the step height required for overcoming an obstacle of a determined height.

In a preferred embodiment of the present invention, the system of the invention can be used in combination with a pharmacological treatment for further facilitating locomotor functions. In particular, the combination of the system with pharmacological treatment provides for a synergistic effect on locomotor functions. In particular, a pharmaceutical composition comprising at least one agonist to monoaminergic receptors, in particular to serotoninergic, dopaminergic and adrenergic receptors, can be administered to the subject.

In a further embodiment of the invention the system of the invention is used in combination with a support system. Said support system (apparatus) can be, for example, a treadmill or a robot-assisted body-weight support or a multidirectional trunk support system.

Generally, in the rehabilitation process a subject can start with the system comprising the epidural and/or subdural electrical stimulation of the present invention and the trunk support, and in a subsequent step use only the electrical stimulation.

In a preferred embodiment, said support system is a robotic interface capable of evaluating, enabling and training motor pattern generation and balance in subjects with neuromotor impairments. For a description of said robotic interface reference can be made to the paper "Versatile robotic interface to evaluate, enable and train locomotion and balance after neuromotor disorders." Dominici N, Keller U, Vallery H, Friedli L, van den Brand R, Starkey ML, Musienko P, Riener R, Nat Med. 2012 July; 18(7):1142-7. doi: 10.1038/nm.2845. Further reference can also be made to the paper of van den Brand R, Heutschi J, Barraud Q, DiGiovanna J, Bartholdi K, Huerlimann M, Friedli L, Vollenweider I, Moraud EM, Duis S, Dominici N, Micera S, Musienko P, Courtine G, "Restoring voluntary control of locomotion after paralyzing spinal cord injury", Science, 2012 Jun. 1; 336(6085):1182-5.

Therefore, it is also an object of the present invention a system for restoring voluntary control of locomotion in a subject suffering from a neuromotor impairment comprising the closed-loop system for real-time control of epidural and/or subdural electrical stimulation as described above and further comprising an apparatus selected from the group consisting of a treadmill or a robot-assisted body-weight support or a multidirectional trunk support system.

It is also an object of the present invention, a method for determining optimal stimulation parameters for a subject suffering from a neuromotor impairment and undergoing a process for facilitating locomotor functions comprising the following steps:
  a) determining a first electrical stimulation which has been applied to said subject bearing means for applying an epidural and/or subdural electrical stimulation with adjustable stimulation parameters;
  b) acquiring feedback signals from said subject, said signals being neural signals and/or providing features of motion of said subject, through a real-time monitoring system, while this first stimulation occurs;
  c) transmitting said feedback signals to a signal processing device;
  d) calculating by means of said signal processing device operating a Real Time Automatic Control Algorithm new stimulation parameters;
  e) providing instructions to said means of step a) for applying a second epidural and/or subdural electrical stimulation so that said means are capable to administer a second electrical stimulation with said new stimulation parameters calculated in step d) to said subject.

An optimal stimulation pattern (said pattern being determined by the ensemble of said stimulation parameters) is the pattern which allows obtaining at each gait cycle the desired reference output. Said optimal stimulation pattern is calculated by the signal processing device in step d) thanks to the Real Time Automatic control Algorithm, as above described. In a preferred embodiment, the reference output is a step height of a limb of the subject defined by the operator of the method and the optimal stimulation pattern is the one which allows the obtainment of said step height. In another preferred embodiment, the reference output is the trajectory of the subject foot height over time and the optimal stimulation pattern is the one which allows the obtainment of said trajectory.

In a preferred embodiment, in step b) 3D coordinates from said subject are acquired, preferably coordinates of one or more of hip, knee, ankle and foot. Acquisition of foot coordinates is preferred, even more preferred is acquisition of step height.

Such configuration provides the maximum strength to stepping in terms of ground reaction forces, muscle activation and support of body weight, while minimizing coactivation.

In another embodiment, in step b) cortical signals from the sensory, motor, sensorimotor or pre-motor cortex are acquired as feedback signals.

Preferably, adaptive fitting algorithms are used, preferably adaptive fitting algorithms that take into account fatigue and time-varying characteristics of the locomotor system.

Generally, said first electrical stimulation has a frequency comprised between 5 and 120 Hz, preferably it is comprised between 25 and 95 Hz.

In one embodiment, said Automatic Control Algorithm in step d) comprises a feedback component and a feedforward component.

Said feedback component compensates for modeling errors or unexpected disturbances, as explained above for the system used to carry out this method.

In one embodiment, said stimulation pattern of step e) comprises a second stimulation frequency which is calculated by said feedback component according to the formula 1 above.

In one embodiment, said feedforward component employs an input-output model which is a single input-single output model (SISO), wherein one stimulation feature is changed to control one gait feature, or, alternatively a multiple input-single output (MISO) model, wherein multiple stimulation features are controlled to obtain a single desired gait feature (output). For a detailed explanation, see above in connection with the system of the present invention.

Another object of the present invention is a method for facilitating standing and walking functions in a subject suffering from neuromotor impairment comprising the following steps:

a) using a system for restoring voluntary control of locomotion comprising the closed-loop system as above described;

b) providing to said subject a first epidural and/or subdural electrical stimulation with adjustable stimulation parameters;

c) acquiring feedback signals from said subject, said signals being neural signals and/or providing features of motion of said subject;

d) transmitting said feedback signals to a signal processing device;

e) calculating by means of said signal processing device operating a Real Time Automatic Control Algorithm new electrical stimulation parameters;

f) providing to said subject a second electrical stimulation with said new electrical stimulation parameters calculated in step e), and optionally g) administering to said subject before and/or during administration of said first and/or said second electrical stimulations a pharmaceutical composition comprising at least one agonist to monoaminergic receptors.

In one embodiment, in step e) said Real Time Automatic Control Algorithm comprises a feedforward component employing an input-output model which is a single input-single output model (SISO), wherein one stimulation parameter is changed to control one gait feature, or, alternatively a multiple input-multiple output (MIMO) model, wherein multiple stimulation parameters are adjusted to obtain a single desired gait feature (output).

In particular, the combination of controlled epidural and/or subdural electrical stimulation applied using the closed-loop system of the invention with a robotic training and optionally also with a pharmacological stimulation allows for the restoring of voluntary control of locomotion.

In one embodiment, said acquisition of feedback signals of step c), comprises acquisition of the coordinates of one or more of hip, knee, ankle and foot. Acquisition of foot coordinates is preferred, even more preferred is acquisition of step height.

In another embodiment, said feedback signals acquired in step c) are cortical signals from sensory, motor, sensorimotor or pre-motor cortex.

Generally, said first electrical stimulation has a frequency comprised between 5 and 120 Hz, preferably it is comprised between 25 and 95 Hz.

The invention will be further described by means of examples.

EXAMPLES

Example 1

Effect of Epidural Electrical Stimulation on Bipedal Stepping

Experimental Procedures

All experimental procedures were approved by the Veterinary Office of the Canton of Zurich. The experiments were conducted on 7 adult, female Lewis rats (~220 g). The rats were housed individually on a 12 h light/dark cycle, with access to food and water ad libitum. All spinal cord-injured animals received manual expression of the bladder twice a day and stretching of the hindlimb flexor and adductor muscles once a day to prevent joint contractures. Additionally, all animals were put together into a large cage three times a week to meet their social needs.

After surgeries (complete midthoracic transection of the spinal cord at level T 6/7), two epidural electrodes implanted at spinal segments L2 and S1, and two electromyographic (EMG) electrodes chronically implanted on both legs for the TA (Tibialis Anterioris) and MG (Gastrus Medialis) muscles), all rats were allowed to recover for 5 weeks to regain stable levels of excitability in the spinal networks to facilitate locomotion via EES (Musienko, P., Heutschi, J., Friedli, L., den Brand, R. V. & Courtine, G. Multi-system neurorehabilitative strategies to restore motor functions following severe spinal cord injury. Experimental neurology, doi:10.1016/j.expneurol.2011.08.025 (2011); Keller. Construction and Control of a Multi-Directional Support System for Neurorehabilitation of Spinal Cord Injured Rats. Master Thesis in Mechanical Engineering, ETH Zürich (2009)). Treadmill training was performed every other day for 30 minutes starting from day 9 post surgery (P9). EES frequencies during training were kept constant at 40 Hz.

Figure 1:
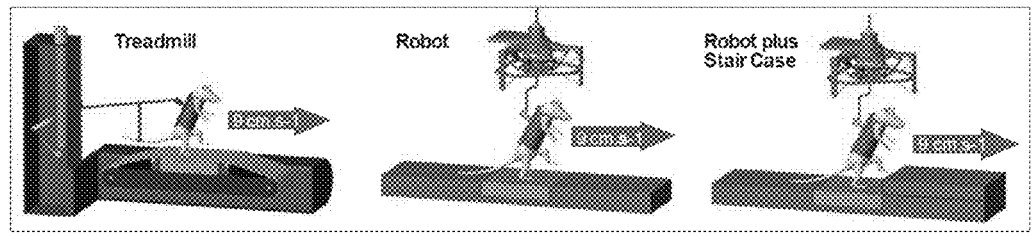
FIG. 1 shows tasks performed in the presence of EES and pharmacologic agents: Treadmill, Overground (Robot-assisted body-weight support), or functional applications on Robot +Staircase.
Figure 2:
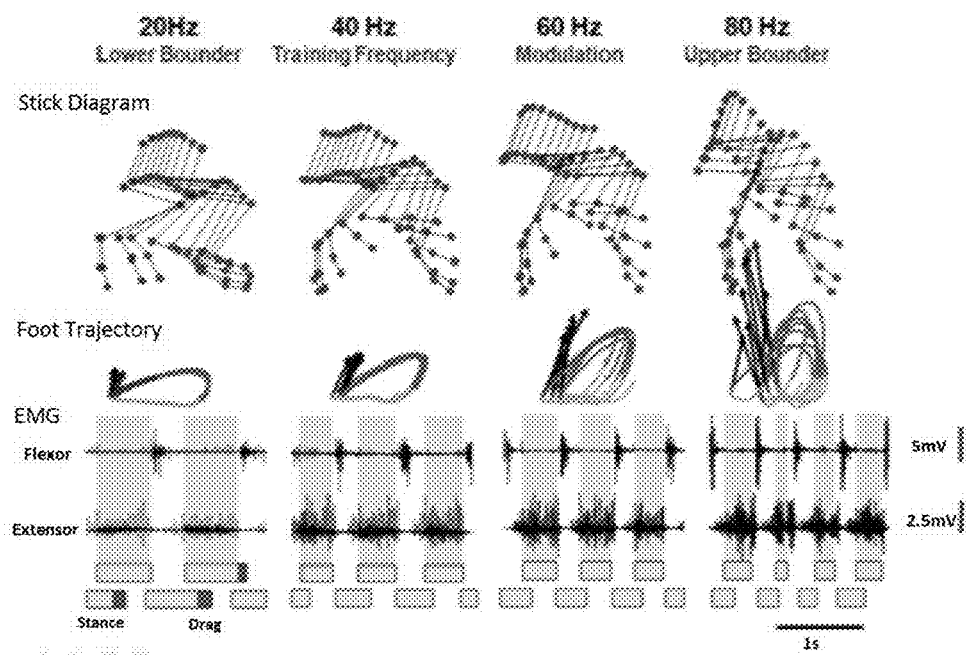
FIG. 2 shows an example of locomotor patterns recorded on treadmill as the frequency of stimulation is modulated from a functional lower limit (dragging occurs and little ground reaction forces) to a high values where walking becomes little consistent and jumpy.

Recordings were performed on treadmill (constant speed of 9 cm/s) or overground (body-weight robotically assisted—FIG. 1). A robust baseline of locomotor output was recorded for at least ten successive consistent gait-cycles enabled by EES. Stimulation at both S1 or L2 were tested for their modulatory capacities by changing stimulation frequencies in intervals of 5 Hz ranging from 0 to 120 Hz. Pulse-width was kept constant at 0.2 ms. Amplitude was set between 100-300 uA depending on the animal to allow for adequate BWS (Body Weight Support). These parameters were kept constant for the entire recording session.

Frequency Modulation of SISO System

In order to perform the system identification process, we excited the system with varying stimulation parameters and monitored how locomotor patterns are affected.

We focused on the effect of frequency, this parameter having been surprisingly found out as the more effective one. We performed detailed analyses of the kinematic and EMG outputs. A total of 116 kinematic parameters (or "features") were evaluated for each gait cycle, as a way to quantify specific aspects of gait.

We focused at finding relationships in a single-input single-ouput (SISO) configuration, for which the modeling and control process is often straightforward, and which entail that simple relations between inputs and outputs can be directly verified online. Thus both electrodes (S1 and L2)

were coupled and their stimulation changed together. The range of EES frequencies applied during the system identification process ranged from 5 Hz up to a maximum of 120 Hz, after which the consistency of locomotor outputs clearly decayed (e.g., jumping). Within this functional range, we restricted our modeling and further control to work between 25 Hz and 95 Hz. This is because we were particularly interested in the modulation of gait parameters for conditions with a minimum percentage of drag and minimal stepping variability.

Single-Input Single-Output (SISO) Mapping

Data Analysis & Feature Selection

In order to find relationships between stimulation and locomotor features, we performed well-known data dimensionality reduction techniques (Principal Component Analysis) to emphasize correlations between the different features employed to quantify stepping, and to extract specific output parameters that explain a high amount of variance in the data (PCs 1-3 explained up to 49% of variability of the entire data set, hence highlighting clear structures in the data, specifically modulated with the input). Indeed different stimulation conditions generated clustered outputs in PC space (FIG. 3), and this regardless of the inter-animal differences. It thus appears as clear that EES frequency clearly and consistently modulates locomotor patterns across animals in unique and predictive ways. Gait features that were most correlated with changes in EES frequency could be grouped into functional clusters of flexion, extension, speed and variability along PC1.

Foot Height is Linearly Correlated to Stimulation Frequency

The factor loadings revealed that step height (i.e., the maximum height reached by the foot during each gait cycle) is nicely modulated with the input. Their relationship happened to be close to linear and step height is modulated with the input (FIG. 4), which allowed us to build a linear input-output model to be further used for our controller. This appeared as a particularly well suited model for our control purposes.

Example 2

Closed-Loop Control Based on SISO Models

Closed-Loop Monitoring and Control Setup

A Vicon Kinematic System (Nexus) acquired 3D coordinates of reflective marker positions in real time (200 Hz) according to a user-defined kinematic model (markers for: Crest, Hip, Knee, Ankle and Foot, for both legs), built on a per-animal basis for high accuracy tracking. The acquired coordinates were then transmitted through the Vicon Data Stream to an external Personal Computer via an Ethernet port. On the external Personal Computer, our C++ program was programmed to interface simultaneously with the Kinematic Data Stream and the TDT Program Code (RZ5 Bioamp Processor, TDT). The C++ Code was programmed to detect foot-strike in real time and adapt the stimulation using the linear model previously built (FIG. 5), as mentioned in example 1, thanks to the presence of a controller. Thus, a closed-loop control structure has been established.

Controller Structure

The input-output linear model was employed as feedforward component within our closed-loop control structure. This allowed to directly derive the most suited stimulation frequency given the desired reference output at each gait-cycle, and to minimise control delays. We note that the model was also constantly updated using adaptive filtering techniques (Least Mean Squares—LMS) so as to allow the linear input-output mapping to account for time-dependencies or inter-animal differences.

The control structure was complemented with a feedback component (a Proportional Integral (PI) Control part) to compensate for modelling errors or unexpected disturbances not accounted for in our static input-output mapping. The feedback control calculates the "error" value between a measured output variable and a desired reference, and then attempts to minimize it by adjusting the control inputs.

Control corrections were applied at each foot strike. At that instant, the 'real time control thread'—programmed in C++—determined the maximum step height during the previous gait cycle. It evaluated the error with respect to the desired reference value and derived the new stimulation frequency. Formula 1 depicts how the new stimulation frequencies were calculated. The new stimulation frequencies were determined as the sum of a partial correction+an integral correction.

We applied the Proportional Integral Controller in two experimental settings: first on treadmill as a proof of concept, and then on a runway plus stair-case for a more practical-oriented application. In the latter configuration, few steps were available for adapting the feed-forward component; thus, in order to reduce model-based errors, we chose to remove the predictive term (i.e. the feedforward component) and let the feedback loop drive the controller. The correction of stimulation frequencies was consequently based only on the proportional and integral terms of the PI Controller.

Controllability and Model Accuracy

In order to quantify the quality of the usability of our model for closed-loop control, and to verify its accuracy and adaptability over time, we designed specific control tasks to test how the system would behave when pushing the limits of the system.

The first test involved constant changes in the desired reference (changes happened at every gait cycle) in order to compel the controller to employ the feed-forward model and hence quantify its accuracy, and its suitability even in situations where the system is pushed to the limit. Together with this, we could analyze how big (and how fast) changes could be applied to the reference with the system following the desired behaviour.

The second test looked at the fine-tuning, and was specifically conceived to evaluate whether the controller could help reducing the inherent variability in bipedal stepping. This was carried by imposing a constant reference, and by narrowing the beam allowed for the stepping.

More details are presented in the next sections.

Evaluation of Feedforward Component—'Scissor Task'

We applied constant changes of reference at constant rates, asking the step-height to constantly increase or decrease following a periodic reference tracking with a triangle waveform Different changing rates were tested to try and quantify the degradation in accuracy as the speed increases.

This task is important because it is mainly driven by the feed-forward component (i.e., the linear model), and it thus allows to quantify to what extent the input-output relationship captures the system response. It further evaluates the behaviour of the system under limit conditions, in which the step-heights need to be adapted at fast changing rates. FIG. 6 underlines the astonishing accuracy of the model, no matter how fast the system was required to change (No statistical difference was found between the errors under the different conditions).

Evaluation of Feedback Component—Fine Tune of Stepping Variability

Our second experimental condition was a "constant reference" task, in which the step-height was required to maintain a constant level over 48 consecutive steps. This framework, mostly driven by the feedback component, focuses on whether our controller also allows reducing the inherent variability in stepping, i.e. to fine-tune the output.

For this matter, the beam (within which variability is allowed) was constantly reduced, thereby forcing the controller to try and correct for more steps that fall outside of the allowed range (FIG. 7 shows an example of the beam being reduced from +/−5 mm to +/−1 mm each 48 gait-cycles).

FIG. 8 outlines the statistical results for healthy (black), non-controlled (white) and controlled (grey—different beams indicated in the x-axis label, from +/−1 mm to +/−8 mm). Big values for the beam (e.g., +/−8 mm) resulted in a variability in the range of what is observed in non-controlled animals (since no steps fall outside of the beam and thus no control is actually acting). The variability is slightly reduced after +/−6 mm, and reaches a plateau that is kept even when trying to reduce the beam.

Example 3

Functional Applications

Fighting Fatigue for Improved Rehabilitation.

We then tested the capacity of the presented model and controller to be employed for applications that might prove useful form a rehabilitation perspective.

One of the major motivations that underlie controlled electrical stimulation, either when referring to EES or FES (Functional Electrical Stimulation), is that it may help to compensate for the fatigue that often derives from an external source of muscle activity. In the framework of EES-induced locomotion, fatigue yields a decreased flexion and extension pattern during stepping over time, and hence inducing lower stepping and eventually collapse.

Here we tested whether the present controller could be employed to ensure that consistent stepping heights are maintained over time, as a way to fight fatigue. We quantified the duration of good stepping in both controlled and non-controlled (constant 40 Hz) trials, and we show (FIG. 9) that time of good stepping allowed by the controller was increased 5-fold with respect to the non-controlled situation. The full length of trials were also extended almost two times (reported results are on n=3 animals).

Climbing Stairs

Our second application, which appeared as a natural step forward in the evaluation of our controller, was to quantify its applicability for climbing stairs. Animals were walking overground, and were asked to climb stair-cases of 3 different heights (small 13 mm, medium 20 mm and high 30 mm) as a way to accurately quantify our capacity to control the modulation appropriately depending on the requirement of the situation, i.e., the controller was set to precisely adapt the animal stepping so as to overcome the obstacle at 30 mm above the stair (FIG. 10). Interestingly, the force exerted on the force-place also shows marked modulation as frequency is increased.

Example 4

MIMO Models for Exploiting Multi-Site Stimulation

The feedback controller aforementioned has pointed out the capacity to control one feature of gait by changing one characteristic of stimulation (frequency at both S1 and L2 together). It is however our contention that the spinal cord is composed of widely distributed, yet highly synergistic neural circuits that can generate a variety of movements when recruited in a task-specific manner.

Time-Encoded Output & Biomechanical States

Extending the previous feedback controller to multi-site stimulation (in a 'multiple-input single-output' (MISO) approach), requires controlling each single site independently based on a measure of error in the output. The main challenge is to determine how to update each individual electrode based on a single error value. Interestingly, depending on their location, certain epidural electrodes affect motor output mostly during 'flexion' (at the beginning of swing), whereas others are mostly responsible for 'extension' (during the end of swing and stance). The output however will be considered over the whole swing phase, i.e. the trajectory of the foot height over time. This trajectory may be parameterized (for instance, through a polynomial fitting of degree N:

$$y(t) = \sum_{i=0}^{5} w_i t^i + \epsilon, t \in [0, 1]$$
$$\equiv [w_0, \ldots w_5], t \in [0, 1]$$

Which captures time-information in a few parameters $w_i$ to which each stimulation input contributes (FIG. 11a-left).

In addition given the effect that biomechanics play on stepping, we increased our input description to account for body position (kinematics—FIG. 11b, right) and kinetics: we accounted for angular positions and speeds of the three joint angles in each leg (Hip, Knee and Ankle) along with Ground Reaction Forces in our model, and employ them at each gait-cycle to derive the most suitable stimulation given the current biomechanical state.

At each foot-strike, the built model then allows to derive the best stimulation strategy for each electrode independently, so as to generate in the output a foot trajectory that is closer to what is desired. The model was built on 554 samples, and validated via 10-fold cross-validation (FIG. 12).

Conclusion

We have uncovered highly consistent linear relationships between the frequency of EES and relevant parameters of gait (step height). The robustness of these relationships allowed us to develop forward models and control algorithms that achieved real-time control of locomotion in rats with complete SCI. The linear mapping between these variables greatly simplified the requirements for the controller. A single input-single output closed loop system was sufficient to achieve the precise control of foot trajectory during complex locomotor tasks in rats with complete SCI. We thoroughly evaluated the degree of controllability of the system, and revealed unexpected performances that were highly consistent across animals, tasks, and time.

Together, these results highlight the potential of real-time control systems to optimize EES-induced locomotion. The core principles underlying our monitoring and control systems may be condensed to fairly simple, wearable hardware. The translational application of our methods for real-world applications could rely on a gyro attached to the foot of the subject, a foot-strike detector (e.g., a force-based switch) and an onboard microcontroller that reads position and calculates proportional frequency-corrections online.

Example 5

Phase-Dependent Triggering of Specific Electrodes for Promoting Flexion or Extension During Locomotion.

In combination with the aforementioned control of frequency, specific electrodes may be turned ON and OFF to mimic the phase-dependent activation of sub-circuits in the spinal cord, namely those related to whole-limb extension (which are mostly active during stance, and whose motor pools are mostly located along sacral spinal segments) and those related to whole-limb flexion (usually active during swing, and motor pools located in lumbar spinal segments).

Based on this premise, using multi-electrode arrays, we have developed a physiologically-relevant stimulation paradigm that accurately triggers electrodes located at lumbar or sacral regions during swing and stance respectively. Based on real time feedback algorithms that flexibly detect specific key events of gait, we alternatively activate specific electrodes at exactly the right sup-phases of gait and induce stronger gait patterns, which translate into stronger muscle activation (even for muscles which otherwise get almost no activation), stronger ground reaction forces and more prominent kinematic patterns.

In our design, we uncovered that optimal stimulation timings include:
- Triggering sacral electrodes (S1) at footstrike (kinematic event that defined the beginning of stance) and maintaining the electrode active at least until the end of activity the tibialis anterior muscle (once swing has been initiated).
- Likewise, lumbar electrodes (L2) need to be turned ON before the activation of the tibialis anterior muscle (before the beginning of swing) and be active at least until mid-swing (preferably until footstrike).

Such configuration provides the maximum strength to stepping in terms of ground reaction forces, muscle activation and support of body weight, while minimizing coactivation.

Example 6

Triggering of Spinal Electrodes Based on Cortical Recording for Promoting Voluntary Locomotion.

Referring to previous examples 1-5, the aforementioned controllers of frequency and timing of stimulation can be connected to the voluntary motor intention of the subject animal.

By using a real-time electrophysiology workstation and 32-channel micro-wire electrode arrays (Tucker-Davis Technologies, Alachua, Fla., USA) implanted in the rats' sensorimotor cortex hind-limb area, in a single hemisphere or in both, we could collect information about the animal's locomotor state, encoded as neuronal multi-unit (MU) activity.

We reliably discriminated the motor intention of the rat into two behavioral states, 'rest' or 'walk', using either un-supervised or semi-supervised machine learning approaches that resulted in intention decoding with 50-100 ms time granularity.

The decoding of the motor intention of the rat is immediately (within 50 ms) fed to the supervision of spinal stimulating electrodes, switching ON the feedback-feedforward controller and thus achieving the desired locomotor pattern. An exemplary representation of the system of the invention is represented in FIG. 15 and explained in its caption.

Moreover, in case the spinal cord lesion does not involve the entirety of the fibers of the pyramidal tract, we have found that kinematic sensorimotor information modulating with the gait pattern is still visible in the recording of the hindlimb sensorimotor cortex, during both treadmill and over-ground recordings. This is, for instance, the case of a severe spinal cord contusion, as shown in FIG. 15.

Cortical recordings contain information related to the gait cycle and can be used to control or refine in real time the triggering of spinal electrodes, respectively substituting or co-operating with the kinematic-feedback algorithms aforementioned.

Example 7

Subdural Adaptive Electrical Spinal Cord Stimulation Resolves Limb-Specific Impairments After Unilateral Spinal Cord Injury The same experimental procedure described in Example 1 has been performed implanting subdural electrodes instead of epidural electrodes and applying a subdural electrical stimulation. All the other experimental parameters were the same as in example 1.

Computerized simulation showed increased selectivity of unilateral voltage fields for subdural implantation (FIG. 16A).

As shown in FIG. 16B, electrophysiological experiments confirmed that subdural stimulation required reduced current threshold, and achieved more specific unilateral recruitment of motor neurons compared to epidural stimulation.

Subdural spinal cord stimulation delivered through the lateral electrodes of a soft subdural implant (40 Hz, 0.2 ms, 20-50 µA) promoted coordinated, weight bearing plantar stepping of the paralyzed hindlimb with improved gait characteristics compared to continuous stimulation (FIGS. 17B-17C).

Subdural adaptive electrical spinal cord stimulation can also be applied for bilateral limb paralysis after motor complete spinal cord injury.

The invention claimed is:

1. A closed-loop system for real-time control of epidural and/or subdural electrical spinal cord stimulation comprising:
   an electrical stimulation device for applying to a subject neuromodulation with adjustable stimulation parameters, said electrical stimulation device being operatively connected with:
   a real-time monitoring component comprising sensors continuously acquiring feedback signals from said subject, said feedback signals being neural signals and/or signals providing features of motion of said subject, said feedback signals providing information on subject kinematics including a limb and/or joint trajectory and/or an angle of one or more extremities of the subject, and where said feedback signals are used to detect gait events based on signals indicative for foot elevation to detect foot-strike events and toe-off events, thereby defining sub-phases of gait, where the sub-phases include at least one of a stance-phase and a swing-phase, said system being operatively connected with:
   a signal processing device receiving said feedback signals and operating real-time automatic control algorithms, said signal processing device being operatively connected with said electrical stimulation device and providing said electrical stimulation device with new stimulation parameters, with minimum delay, said signal processing device being operatively connected with:

a controller comprising a feedforward component and a feedback component, which allows for directly deriving a desired electrical stimulation given a desired gait feature at each gait-cycle, and to minimize control delays.

2. The system of claim 1, wherein said electrical stimulation device comprises an epidural and/or subdural electrical stimulation device.

3. The system of claim 1, wherein said stimulation parameters are selected from the group consisting of waveform, amplitude, pulse width, and frequency.

4. The system of claim 2, wherein said electrical stimulation device comprises one or more electrodes or an electrode array.

5. The system of claim 4, wherein said electrical stimulation device also comprises an implantable pulse generator.

6. The system of claim 1, wherein said electrical stimulation device provides a stimulation frequency between 5 and 120 Hz and with a resolution of 1 Hz.

7. The system of claim 1, wherein said electrical stimulation device provides phasic stimulation or burst stimulation.

8. The system of claim 1, wherein said electrical stimulation device is applied to at least two stimulation sites and each stimulation site can be independently turned on or off.

9. The system of claim 4, wherein said electrical stimulation is location-specific and wherein stimulation parameters of each individual electrode can be independently modified in real-time.

10. The system of claim 1, wherein said electrical stimulation device comprises electrodes applied on sacral and lumbar sites which are alternatively activated to promote, respectively, whole-limb extension or flexion.

11. The system of claim 1, wherein said real-time monitoring component comprises limb position markers or sensors.

12. The system of claim 1, wherein said feedback signals acquired by said real-time monitoring component are neural signals, in particular cortical signals, recorded from sensory, motor, sensorimotor, or pre-motor cortex.

13. The system of claim 1, wherein said feedback signals acquired by said real-time monitoring component are both neural signals and signals providing features of motion of said subject.

14. The system of claim 1, wherein said signal processing device operates a program comprising an automatic control algorithm that interfaces simultaneously with data flow from said real-time monitoring component and the electrical stimulation device for neuromodulation in real-time.

15. The system of claim 1, wherein the desired gait feature includes a desired step height of one or more feet of the subject, where step height of the one or more feet of the subject is acquired as feedback signals via the real-time monitoring component and received via the signal processing device, for directly deriving the desired electrical stimulation given the desired step height of the one or more feet of the subject at each gait-cycle via the controller.

16. The system of claim 15, wherein the step height comprises a maximum height reached by the one or more feet of the subject during each gait-cycle as monitored via the real-time monitoring component.

* * * * *